United States Patent
Fujiwara et al.

[11] Patent Number: 5,858,971
[45] Date of Patent: Jan. 12, 1999

[54] CYCLIC PEPTIDE AND METHOD OF MAKING SAME BY CULTURING A STRAIN OF ACTINOMYCES *S. NOBILIS*

[75] Inventors: Akihiko Fujiwara; Kiyoshi Kuriyama; Yoshiko Abe; Koji Inagaki, all of Osaka, Japan

[73] Assignee: Sekisui Chemical Co., Ltd., Osaka, Japan

[21] Appl. No.: 809,406

[22] PCT Filed: Oct. 25, 1994

[86] PCT No.: PCT/JP95/02187

§ 371 Date: Apr. 22, 1997

§ 102(e) Date: Apr. 22, 1997

[87] PCT Pub. No.: WO96/12732

PCT Pub. Date: May 2, 1996

[30] Foreign Application Priority Data

| Oct. 25, 1994 | [JP] | Japan | 6-260324 |
| Oct. 25, 1994 | [JP] | Japan | 6-260325 |
| Oct. 25, 1994 | [JP] | Japan | 6-260326 |
| Oct. 25, 1994 | [JP] | Japan | 6-260327 |
| Mar. 2, 1995 | [JP] | Japan | 7-042927 |
| Apr. 24, 1995 | [JP] | Japan | 7-098605 |

[51] Int. Cl.$^6$ .......................... A61K 31/00; A61K 38/12; C12P 21/04
[52] U.S. Cl. .............. 514/9; 530/317; 435/71.1
[58] Field of Search .................. 530/317; 514/2, 514/9; 435/68.1, 252.35, 252.1, 71.1, 71.2, 71.3

[56] References Cited

FOREIGN PATENT DOCUMENTS

| 05025053A | 2/1993 | Japan . |
| 5-25053 | 2/1993 | Japan . |
| 06172194A | 6/1994 | Japan . |
| 6-172194 | 6/1994 | Japan . |
| 06247863A | 9/1994 | Japan . |
| 6-247863 | 9/1994 | Japan . |

OTHER PUBLICATIONS

Nakagawa, M. "A New Depsipeptide Antibiotic, Variapeptin", Agric. Biol. Chem. 1990, vol. 54, No. 3, pp. 791–794.

Nakagawa et al. "Structural studies of new depsipeptide antibiotics, variapeptin and citropeptin," J. Antibiotics (1990) 43(5): 477–84.

*Primary Examiner*—Jon P. Weber
*Assistant Examiner*—Susan Hanley
*Attorney, Agent, or Firm*—Nikaido, Marmelstein, Murray & Oram LLP

[57] ABSTRACT

The present invention relates to a peptide represented by formula [I]. The peptide of the present invention exhibits allergic and anallergic inflammation inhibitory, antibacterial, antitumor and wound-healing effects, and it is useful as an inflammation inhibitor, immunosuppressive agent, antibacterial agent, antitumor agent, wound-healing agent, antiulcer agent, and so forth. Accordingly, the present invention also provides therapeutic agents having the above-mentioned pharmacological effects.

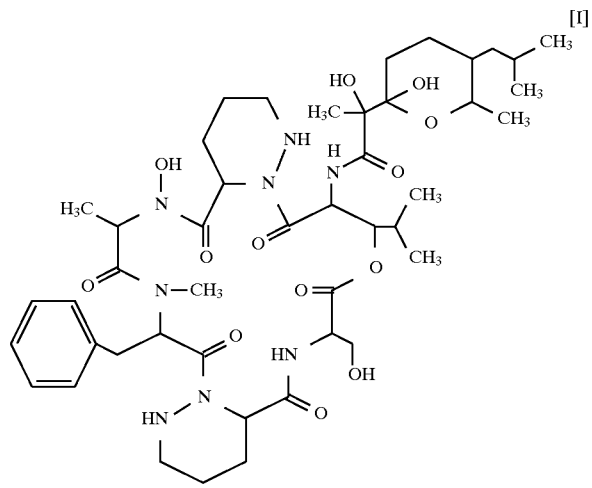

19 Claims, 8 Drawing Sheets

* p<0.05 SIGNIFICANTLY DIFFERENT FROM CONTROL
*** p<0.001 SIGNIFICANTLY DIFFERENT FROM CONTROL

** p<0.01 SIGNIFICANTLY DIFFERENT FROM OLCENON OINTMENT
*** p<0.001 SIGNIFICANTLY DIFFERENT FROM OLCENON OINTMENT

CYCLIC PEPTIDE AND METHOD OF MAKING SAME BY CULTURING A STRAIN OF ACTINOMYCES S. NOBILIS

This application is the National Stage of International Application No. PCT/JP95/02187, filed on Oct. 25, 1995.

1. Technical Field

The present invention relates to a novel peptide. The novel peptide of the present invention exhibits allergic and anallergic inflammation inhibitory, antibacterial and wound-healing effects, and it is useful as an inflammation inhibitor, immunosuppressive agent, antibacterial agent, wound-healing agent, antiulcer agent, and so forth. Accordingly, the present invention also relates to therapeutic agents having the above-mentioned pharmacological effects.

2. Background Art

It is known that an extracted mixture which is obtained by extracting with an organic solvent from a culture medium of *Actinomyces Streptomyces nobilis* (hereinafter referred to as "*S. nobilis*") or a dried product thereof contains a substance having an allergic anti-inflammatory effect (Japanese Laid-open Patent Publication No. 25053/1993).

However, the chemical structure of the substance having the above-mentioned pharmacological effect has not been clarified yet.

A first object of the present invention is to clarify the structure of the substance and to provide a novel peptide.

More than 5,000 kinds of antibiotics produced by microorganism have been reported so far. Among them, streptomycin, actinomycin C, actinomycin D, etc. originating from microorganisms belonging to Streptomyces genus have been reported.

In using antibiotics, appearance of resistant bacteria brings about problems and new types of antibiotics are desired.

Accordingly, a second object of the present invention is to provide a novel antibiotic having a high antimicrobial activity.

Inflammations are classified into anallergic inflammation and allergic inflammation. Non-steroidal anti-inflammatory agents such as aspirin (Nikkei Science, 3, 70 (1991)) and indomethacin (Ther. Res., 3, 1057 (1985)), and steroidal anti-inflammatory agents such as prednisolone are effective against anallergic inflammation represented by carrageenin edema. On the other hand, allergic inflammations are classified into types I–IV. Type I reaction participates in various allergic diseases such as atopic dermatitis, asthma, rhinitis and the like. Type II reaction, type III reaction (immune complex reaction: Arthus reaction) and type IV reaction (cell immunity reaction: delayed type hypersensitive reaction) have been found to play important roles in the crisis and the development of autoimmune diseases such as rheumatoid arthritis and various inflammatory diseases such as hepatitis, nephritis, dermatitis, infectious disease, hemolytic anemia and insulin-dependent diabetes mellitus. Steroid anti-inflammatory agents such as prednisolone are effective against these allergic inflammations.

The steroid anti-inflammatory agents which are effective against allergic inflammation have defects in side effects such as drop in phylaxis function, digestive tube disorder, inhibition of hypophysis-adrenal function and drop in osteogenesis. There is a problem that the non-steroid anti-inflammatory agents which are considered to be safer than the steroid agents have very low inhibitory effects on allergic inflammation. Accordingly, an anti-inflammatory agent which is highly effective and less toxic is desired.

In view of the above-mentioned points, a third object of the present invention is to provide a novel anti-inflammatory substance which is effective against allergic inflammation and anallergic inflammation and useful.

Wounds are injuries of surface tissue such as surgical incisions, an digestive tube ulcers, burns, lacerated wounds and skin ulcers (such as bedsores). A usual treatment for wounds is to give first aid to an injured sites and then to wait for the injured sites to heal by natural recuperative power of a living body. However, recovery of the injured sites takes a long period of time and patient's pains such as aches are by no means easy matter. Accordingly, it is desired to promote the healing positively and directly without relying on spontaneous recovery. It is considered that the healing of wounds generally depends on the formation of new connective tissue and epithelial tissue by cell proliferation and that a medicine stimulating or promoting the cell differentiation process and the cell proliferation process participating in the healing of wounds is effective.

An extract from blood of young calves (Solcoseryl) (Pharmacometrics, 22,565–579 (1981)), lysozyme chloride, etc. have so far been reported as substance exhibiting promoting effects on the healing of wounds.

However, since wounds such as injuries of surface tissue are generally intractable, any existing medicines hardly exhibit sufficient clinical effects on the wounds.

In view of the above-mentioned points, a fourth object of the present invention is to provide a more useful novel wound-healing substance.

SUMMARY OF THE INVENTION

The present invention provides a novel peptide represented by the formula [I] (hereinafter referred to as "the peptide of the invention").

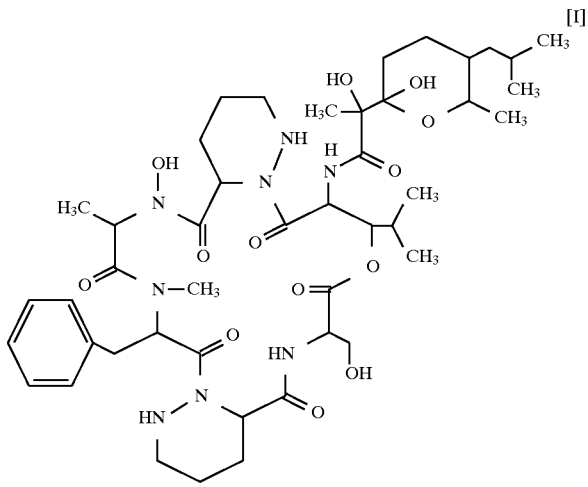

The peptide of the invention is obtained, for example, by purifying an extract which is extracted with an organic solvent from a culture medium obtained by culturing *Actinomyces S. nobilis*, a dried product of the medium or the cultured bacterium by various column chromatography, and, if necessary, by recrystalizing a column chromatography fraction containing the desired product.

*Actinomyces S. nobilis* producing the peptide of the invention is available from some public preservation organizations. There can be used, for example, a preserved bacterium of the Institute of Physical and Chemical Research (JCM4274) (also preserved under ATCC19252 in the United States and under CBS198.65 in the Netherlands), etc.

DETAILED DESCRIPTION OF THE INVENTION

*Actinomyces S. nobilis* is cultured using a medium containing proper nutrition. In case of liquid culture, there can be preferably used an aqueous solution containing one or some kinds of sugars such as glucose, proteins such as peptone and a malt extract, vitamins, nucleic acids, amino acids and complex carbohydrates as components of the medium. A representative example of the medium is a type of starch-ammonium liquid medium (containing soluble starch, $K_2HPO_4$ and $NH_4Cl$). The pH of the liquid medium is preferably 2 to 9 and the culture temperature is preferably 15° to 42° C. The culture period of the liquid culture is preferably 1 to 14 days. The peptide of the invention is extracted with a solvent from the culture medium of S. nobilis obtained in such manner, the dried product thereof or the bacterium itself.

The extract of the culture medium of S. nobilis, the dried product thereof or the bacterium itself may be treated with ammonium sulfate and the obtained precipitate may be extracted with a solvent. In treating with ammonium sulfate, ammonium sulfate to be added to the extract of the culture medium, the dried product thereof or the bacterium itself may be both in solid and in solution thereof. The amount of ammonium sulfate to be added is preferably in the range of 30 to 90% by weight of the saturated concentration. The treatment time is preferably in the range of 30 minutes to 5 hours, but it is not limited thereto. In centrifuging to obtain the precipitate, the centrifugal force is preferably 3,000 G to 20,000 G and the centrifugation time is preferably 2 to 60 minutes.

Organic solvents are preferable as the solvents used for the extraction. Representative examples of the organic solvents are esters such as ethyl acetate, alcohols such as methanol, ethanol and propanol, ethers such as ethyl ether and dioxane, ketones such as acetone and methyl ethyl ketone, dichloromethane, chloroform, etc. However, usable solvents are not limited to them. A mixture of the above-mentioned solvents can be also used. Preferred solvents are ethyl acetate, dichloromethane, acetone, etc. The extraction time varies with kind of the solvent, extraction temperature, etc., but it is preferably in the range of 3 to 120 minutes. The liquid may be both allowed to stand and stirred during the extraction. The extraction operation is preferably repeated several times with respect to one sample. The extraction temperature is not particularly limited.

Next column chromatography for the solvent extract is described.

As a filler for column chromatography, silica gel modified with ODS (octadecylsilanes such as octadecyldimethylchlorosilane) (hereinafter referred to as "ODS silica gel") is preferable. The filler content is not particularly limited but it is preferable to charge the filler having a weight 10 to 500 times as much as the solvent extract to be charged. In charging the solvent extract into a column, it is preferable to first make the solvent extract adsorb on the ODS silica gel. The amount of the ODS silica gel is not particularly limited either, but it is preferable to make the solvent extract adsorb on ODS silica gel having a weight 0.5 to 20 times as much as the extract, to suspend the ODS silica gel adsorbing the extract in a small amount of a solvent and to charge the suspension into the column. The elution solvent is not particularly limited either, but it is preferable to use solvents having polarity between a 70% aqueous solution containing a mixed solvent of methanol-acetonitrile (1:1) and methanol-acetonitrile-water (19:19:2).

Next purification of the peptide of the invention by recrystalization is described.

Solvents used for recrystalization are not particularly limited so long as they dissolve the peptide of the invention, but methanol, ethanol, etc. are preferable. As a method of recrystalization, a column elution fraction containing the desired substance may be dissolved in a small amount of a solvent upon heating followed by cooling the obtained solution gradually to recrystalize the substance. Alternatively, the column elution fraction containing the substance may be also dissolved in a solvent which easily dissolves the substance, followed by adding a liquid which hardly dissolves the substance (for example, water) to the solution gradually to recrystalize the substance.

As demonstrated by the pharmacological test mentioned below, the peptide of the invention exhibits allergic and anallergic inflammation inhibitory effects, an antibacterial effect particularly being effective for inhibition of proliferation of Gram-positive bacterium and a wound-healing effect, and it is useful as an inflammation inhibitor, immunosuppressive agent, antibacterial agent, wound-healing agent, antiulcer agent, and so forth.

To prepare the above-mentioned therapeutic agents, the peptide of the invention is usually formulated into a preparation composition with a carrier for preparation. Examples of the carriers are a filler, a disintegrator, an extender, a binder, a colorant, a flavor, a pH adjustor, a solubilizer, a suspending agent, a buffer agent, a stabilizer, a preservative, a humectant, a surfactant, a lubricant, an excipient, an antioxidant, a dispersant, a propellant, a dissolvent and a solubilizing agent which are usually used to prepare medicines according to dosage forms. The obtained peptide of the invention can be also used in a liquid preparation form by selecting a suitable solvent.

Examples of dosage forms of the therapeutic agents prepared using the peptide of the invention are tablet, pill, solution for drinking, powder, suspension, emulsion, granule, extract, subtilized granule, syrup, infusion, decoction, eye drop, troche, poultice, liniment, lotion, ophthalic ointment, plaster, capsule, suppository, injection (e. g., liquid preparation and suspension), adhesive tape, ointment, jelly, pasta, inhalant, cream, spray, collunarium and aerosol other than the above-mentioned liquid preparation.

The amount of the peptide of the invention to be contained in the therapeutic agents is not particularly limited and appropriately selected over a wide range. Preferred amount of the peptide is in the range of $10^{-7}$ to 10% by weight in the therapeutic agents.

The therapeutic agents obtained from the peptide of the invention are administered by methods according to various forms when used. For example, external preparations are directly sprayed, applied or spread to required sites such as skin and mucosa. Tablets, pills, solutions for drinking, suspensions, emulsions, granules and capsules are administered orally. Injections are administered intravenously, intramuscularly, intracutaneously, subcutaneously, intraarticularly and intraperitoneally. Suppositories are administered intrarectally.

The dosage of the therapeutic agents obtained from the peptide of the invention is appropriately adjusted depending on purpose, symptoms, etc. The usual daily dosage is in the range of about 10 pg/kg to about 10 mg/kg as the peptide of the invention. Of course, the above-mentioned preparation composition can be administered in one to four divided doses per day.

BEST MODE FOR CARRYING OUT THE INVENTION

EXAMPLE 1

Figure 1:
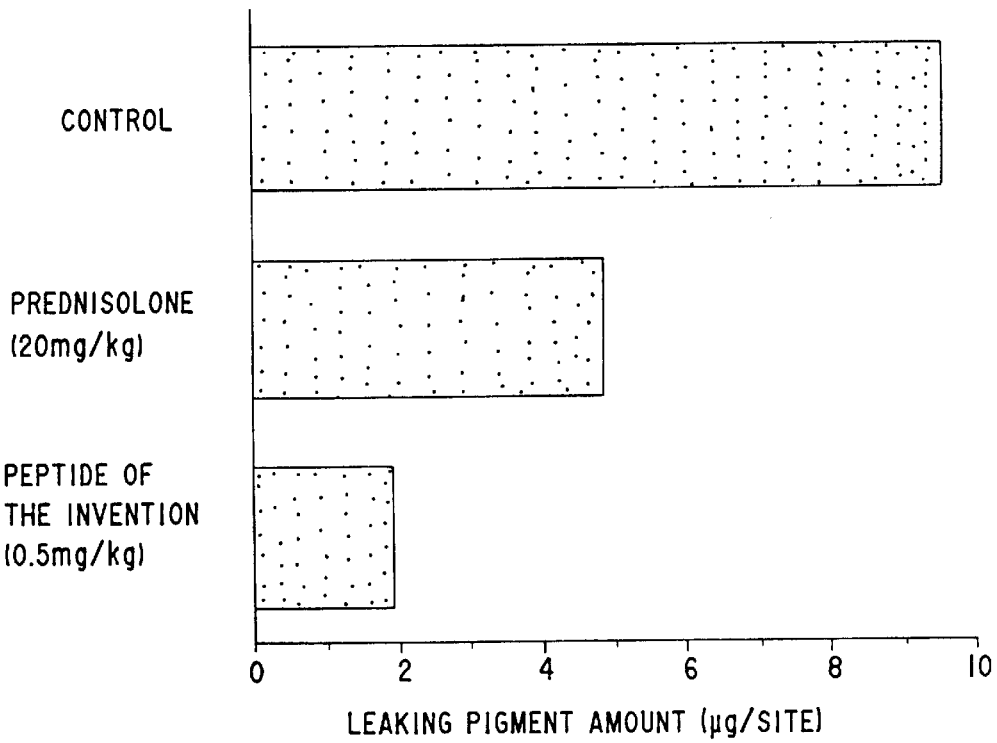
FIG. 1 is a graph showing leaking pigment amount sin rat 48-hour homologous PCA reaction by administering intraperitoneally 0.5 mg/kg of the peptide of the invention, 20 mg/kg of prednisolone and a control thereof respectively.

*Actinomyces S. nobilis* (JCM4274) which had been obtained from the Institute of Physical and Chemical Research was shaking-cultured (pre-preculture) for 40 hours in 100 ml of a starch-ammonium medium to which a 0.2% yeast extract had been added. Then 3 liters of the medium was inoculated with 60 ml of the pre-precultured bacterium liquid, and the mixture was shaking-cultured (seed culture) for 25 hours. In addition, 285 liters of a starch-ammonium medium (containing 1 g of soluble starch, 0.05 g of dipotassium hydrogenphosphate and 0.05 g of ammonium chloride in 100 ml of distilled water) was inoculated with the whole amount of the seed-cultured medium, and the mixture was shaking-cultured at about 30° C. for 8 days. The culture medium was centrifuged. Ammonium sulfate was added to 250 liters of the obtained supernatant at a rate of 662 g per 1 liter of the supernatant and the mixture was stirred for 1 hour. The mixture was then continuously centrifuged at 20,000 G(flow rate: 360 to 500 liters/hr) to give about 12 kg of a precipitate.

To 1.2 kg of the precipitate obtained by the above-mentioned method was added 3.6 liters of water and the mixture was stirred at 80° C. for 30 minutes. An equal amount of ethyl acetate was added thereto, and the mixture was shaked for 10 minutes, followed by centrifuging the whole at 5,000 G for 10 minutes. After separating the ethyl acetate layer, the aqueous layer was subjected to this operation several times to give a solvent extract.

Then the solvent extract obtained by the above-mentioned method was adsorbed on 25 g of an ODS silica gel (practically, silica gel modified with octadecyldimethylchlorosilane) sorbent. The sorbent adsorbing the extract was charged on an ODS silica gel sorbent in a column having a diameter of 3.2 cm to prepare an ODS silica gel column. This column had been filled with 275 g of the sorbent, in advance. The extract was purified with the ODS silica gel column under the following condition. The following elution solvents were made to flow in turn at the rate of 10.5 ml/min: (a) 1.5 liters of methanol-acetonitrile-water (7:7:6), (b) 1.2 liters of methanol-acetonitrile-water (8:8:4), (c) 150 ml of methanol-acetonitrile-water (9:9:2), (d) 1 liter of methanol-acetonitrile-water (19:19:2) and (e) 1 liter of methanol. Each eluate was collected every time the composition of the elution solvent was changed. In particular, the elution fraction of methanol-acetonitrile-water (19:19:2) was appropriately fractionated little by little (every 2 minutes) with a fraction collector. Each elution fraction was analyzed with a high-performance liquid chromatograph (manufactured by Hitachi, Ltd., pump: L-6000L-6200, detector: L-3000, column oven: 655A-52) provided with a column (manufactured by Tosoh Corp., ODS-80TM, 4.6 mm in inner diameter and 25.0 cm in length) under the following conditions; detection wave length=210 nm, column temperature=40° C. and flow rate=1 ml/min, using eluents of water-acetonitrile-methanol (6:7:7 (0 minute) to 0:1:1 (30 minutes)). Only fractions containing a peak having a retention time of 18 to 20 minutes were collected as the same fraction (100 mg) among the above-mentioned fractions. The collected fraction was repeatedly recrystalized from methanol-water to give 45 mg of needles.

The structure of this substance was determined to be that represented by formula [I] by various instrumental analysis data.

EXAMPLE 2

*S. nobilis* was cultured in the same manner as in Example 1. To 215 g (wet weight) of the obtained bacterium was added 2.15 liters of dichloromethane and the mixture was subjected to ultrasonication for 30 minutes. To the mixture was further added 8.6 liters of dichloromethane and the whole was stirred at room temperature for 1 hour. After filtering off the bacteria, the obtained filtrate was concentrated to dryness. The dried product of the extract was dissolved in a small amount of hexane and the hexane phase was extracted with methanol three times. The substance being insoluble in hexane and the methanol extract were dissolved in methanol again.

Next the solvent extract obtained by the above-mentioned method was adsorbed on 28 g of an ODS silica gel sorbent. About 30 g of the sorbent adsorbing the extract was charged on an ODS silica gel sorbent in a column having a diameter of 3.2 cm to prepare an ODS silica gel column. This column had been filled with 275 g of the sorbent, in advance. The extract was purified with the ODS silica gel column under the following condition. The following elution solvents were made to flow in turn at the rate of 10.5 ml/min: (a) 1.5 liters of methanol-acetonitrile-water (7:7:6), (b) 1.2 liters of methanol-acetonitrile-water (8:8:4), (c) 200 ml of methanol-acetonitrile-water (9:9:2), (d) 1 liter of methanol-acetonitrile-water (19:19:2) and (e) 500 ml of methanol. Each eluate was collected every time the composition of the elution solvent was changed. In particular, the elution fraction of methanol-acetonitrile-water (19:19:2) was appropriately fractionated little by little (every 2 minutes) with a fraction collector. Each elution fraction was analyzed with a high-performance liquid chromatograph (manufactured by Hitachi, Ltd., pump: L-6000L-6200, detector: L-3000, column oven: 655A-52) provided with a column (manufactured by Tosoh Corp., ODS-80TM, 4.6 mm in inner diameter and 25.0 cm in length) under the following conditions; detection wave length=210 nm, column temperature=40° C. and flow rate=1 ml/min, using eluents of water-acetonitrile-methanol (6:7:7 (0 minute) to 0:1:1 (30 minutes)). Only fractions containing a peak having a retention time of 18 to 20 minutes were collected as the same fraction (840 mg) among the above-mentioned fractions. The collected fraction was repeatedly recrystalized from methanol-water to give 330 mg of the peptide of the invention as needles.

The structure of this substance was determined to be that represented by formula [I] by various instrumental analysis data in the same manner as in Example 1.

Structure analysis data

The instrumental analysis data of the substances obtained in Examples 1 and 2 are shown below.

1. MS
   .ESI-MS: m/z=913.6 (M+H—$H_2O$)$^+$,
   931.6 (M+H)$^+$,
   953.6 (M+Na)$^+$
   .HRFAB-MS
   Found: m/z=913.5079 (M+H—$H_2O$)$^+$,
   m/z=913, 953, 931 (The peak of 913 is main and the peak of 931 is very small.) Calcd for: $C_{45}H_{69}N_8O_{12}$
   m/z=913.5053

2. IR
   IR: 3,400 cm$^{-1}$: —OH, —NH,
   2,900 cm$^{-1}$: alkyl groups,
   1,750 cm$^{-1}$: —C(=O)—O—,
   1,650 cm$^{-1}$: —C(=O)—NH—

3. Amino acid analysis
   D-serine, L-alanine and D-N-methylphenylalanine were detected as hydrolysis products.

4. Compositional formula
   The compositional formula of the novel peptide was found to be $C_{45}H_{70}N_8O_{13}$ by the data of mass spectrometry and the following NMR.

5. NMR (a) Partial structure A

As a result of measurement of HMBC spectrum, a long-range correlation was observed between carbonyl carbon (173.6 ppm) of alanine (Ala) and $CH_3$ (3.04 ppm) of N—$CH_3$-phenylalanine (Phe). Accordingly, the partial structure A was presumed.

(b) Partial structures B and C

Two components having a similar spin system were presumed by $^1H$—$^1H$ COSY, HOHAHA.

(i) NH (4.38 ppm)

$CH_2$ (46.1, 2.89, 3.15 ppm)
   $CH_2$ (21.3, 1.45, 1.63 ppm)
   $CH_2$ (24.2, 1.93, 2.25 ppm)
   CH (51.7, 4.90 ppm)

(ii) NH (3.93 ppm)

$CH_2$ (47.9, 2.56, 3.30 ppm)
   $CH_2$ (21.5, 1.55, 1.66 ppm)
   $CH_2$ (24.4, 1.67, 2.58 ppm)
   CH (52.5, 5.18 ppm)

Since the $^{13}C$ shifts of the components are very close, they are considered to be based on the same structure (residue). In addition, since the $CH_2$ protons are unequivalent, the components can be assumed to have cyclic structure.

Since the shifts agree with those of piperazic acid (Pip) contained in Monamycin, the components were assumed to be Pip (the left part of the partial structure B and the partial structure C).

|  | α | β | γ | δ |
|---|---|---|---|---|
| Pip$^1$) | 49.8 | 24.1 | 21.0 | 47.0 (CDCl$_3$ solution) |
| Found | 52–53 | 24–25 | 21 | 46–48 (CDCl$_3$ solution) |

Furthermore, since a long-range correlation was observed between NH of 6.40 ppm of serine (Ser) and carbonyl of 168.9 ppm of Pip, the partial structure B was assumed.

(1) C. H. Hassall, W. A. Thomas, M. C. Moschidis, J. Chem. Soc., Perkin Trans. I, 1977, 2371 (1977)

(c) Partial structure D

The partial structure represented by the formula of $(CH_3)_2$—CH—CH—CH—NH— was assumed from $^1H$—$^1H$ spin coupling. The partial structure was confirmed by long-range $^1H$-$^{13}C$ coupling. The structure of β-OH-leucine (Leu) was confirmed by spin coupling between carbonyl of 170.6 ppm and CH of 4.88 ppm. β-OH-Leu was assumed to form an ester bond at β position thereof from CH of 5.46 ppm.

The structure of the side chain part (left) of the partial structure D was confirmed by results of measurements of $^1H$—$^1H$ spin coupling, long-range $^1H$-$^{13}C$ coupling and NOE (Nuclear Overhauser Effect).

The partial structure D was assumed by the fact that a long-range correlation is observed among CH of 4.88 ppm and NH of 8.34 ppm of β-OH-Leu, and carbonyl of 177 ppm of the side chain part from long-range $^1H$-$^{13}C$ coupling.

(d) Chemical structure of the novel peptide

The partial structures B and D were found to form an ester bond between Ser and β-OH-Leu by the fact that a long-range correlation is observed between carbonyl of 170.2 ppm of Ser and CH of 5.46 ppm of β-OH-Leu from long-range $^1H$-$^{13}C$ coupling. The partial structure C was found to bond to the carbonyl group of 170.6 ppm of β-OH-Leu by the fact that NOE is observed between CH of 5.46 ppm of β-OH-Leu and NH of 4.38 ppm of Pip (partial structure C), between NH of 8.34 ppm of β-OH-Leu and $CH_2$ of 2.89 ppm of Pip (partial structure C), and between NH of 8.34 ppm and CH of 4.90 ppm of Pip (partial structure C). Since the method of bonding the remaining partial structure A was one way, the chemical structure of the novel peptide was determined.

The above-mentioned structure supported to be correct by the fact that NOE is also observed between NH of 6.40 ppm of Ser and $CH_3$ of 3.04 ppm of N—$CH_3$-Phe.

(e) The results of measurements of NMR are shown below.

Tables 1 and 2 show $^{13}C$ shifts, carbon types and directly coupling $^1H$. Tables 3–5 show $^1H$ shifts, spin-coupling $^1H$ and $^{13}C$, and long-range-coupling $^{13}C$. Tables 6 and 7 show results of measurements of NOE. Tables 8–11 show assignments of $^{13}C$ and $^1H$.

TABLE 1

$^{13}C$ Shift, carbon type and coupling $^1H$

| Carbon No. | $^{13}C$ Shift | Type | Coupling $^1H$ |
|---|---|---|---|
| 1 | 177.0 | >C=O | — |
| 2 | 174.3 | >C=O | — |
| 3 | 173.6 | >C=O | — |
| 4 | 171.9 | >C=O | — |
| 5 | 170.6 | >C=O | — |
| 6 | 170.2 | >C=O | — |
| 7 | 168.9 | >C=O | — |
| 8 | 136.6 | >C= | — |
| 9 | 129.4 | 2'-CH= | 7.25 |
| 10 | 128.3 | 2'-CH= | 7.26 |
| 11 | 126.7 | —CH= | 7.20 |
| 12 | 99.2 | >C< | — |
| 13 | 78.9 | >CH— | 5.46 |
| 14 | 76.8 | >CH— | — |
| 15 | 71.6 | >CH— | 3.74 |
| 16 | 60.7 | —CH2— | 3.49, 4.54 |

TABLE 2

| | | | |
|---|---|---|---|
| 17 | 55.0 | >CH— | 4.88 |
| 18 | 52.5 | >CH— | 4.75 |
| 19 | 52.5 | >CH— | 5.18 |
| 20 | 52.0 | >CH— | 6.47 |
| 21 | 51.7 | >CH— | 4.90 |
| 22 | 50.6 | >CH— | 5.03 |
| 23 | 47.9 | —CH2— | 2.56, 3.30 |
| 24 | 46.1 | —CH2— | 2.89, 3.15 |
| 25 | 40.9 | —CH2— | 0.95, 1.08 |
| 26 | 39.8 | >CH— | 1.10 |
| 27 | 33.9 | —CH2— | 3.02, 3.11 |
| 28 | 29.4 | —CH3 | 3.04 |
| 29 | 29.3 | >CH— | 1.93 |
| 30 | 27.8 | —CH2— | 1.65, 1.74 |
| 31 | 24.7 | >CH— | 1.66 |
| 32 | 24.4 | —CH2— | 1.67, 2.58 |
| 33 | 24.18 | —CH2— | 1.93, 2.25 |
| 34 | 24.16 | —CH3 | 0.893 |
| 35 | 24.13 | —CH2— | 1.75, 1.44 |
| 36 | 21.5 | —CH2— | 1.66, 1.55 |
| 37 | 21.4 | —CH3 | 0.83 |
| 38 | 21.3 | —CH2— | 1.45, 1.63 |
| 39 | 20.0 | —CH3 | 1.375 |
| 40 | 19.7 | —CH3 | 0.890 |
| 41 | 19.3 | —CH3 | 1.02 |
| 42 | 14.9 | —CH3 | 1.01 |
| 43 | 13.0 | —CH3 | 1.14 |

TABLE 3

$^1H$ Shift, spin-coupling $^1H$ and $^{13}C$, and long-range-coupling $^{13}C$

| $^1H$ | Shift (J) | Number | Coupling $^1H$ | Coupling $^{13}C$ | Long-range-coupling $^{13}C$ |
|---|---|---|---|---|---|
| 1 | 9.62 (s) (OH) | 1 | — | — | |
| 2 | 8.341 (d; 10.6) | 1 | H13 | — | C1 |
| 3 | 7.26 | 2 | | C10 | C8, C10 |
| 4 | 7.25 | 2 | | C9 | C9, C11 |
| 5 | 7.20 | 1 | | C11 | C9 |
| 6 | 6.473 (d, d; 7.0, 9.5) | 1 | H22A, 22B | C20 | C4, C27, C28 |
| 7 | 6.46 (br-s) (OH) | 1 | — | — | |
| 8 | 6.398 (d; 7.9) | 1 | H14 | — | C7 |
| 9 | 5.463 (d, d; 9.6, 1.8) | 1 | H13, H27 | C13 | C6, C17, C40, C42 |
| 10 | 5.179 (d; d) | 1 | H25B | C19 | C7, (C32), (C36) |
| 11 | 5.027 (q; 7.2) | 1 | H34 | C22 | C3, C43 |
| 12 | 4.90 | 1 | H26B | C21 | C2, (C34), (C38) |
| 13 | 4.88 | 1 | H2, H9 | C17 | C1, C5, (C29) |
| 14 | 4.751 (d, d; 8.4, 3.7) | 1 | H8, H15B | C18 | C6 |
| 15A | 4.546 (d; 11.7) | 1 | H15B | C16 | C6 |
| 15B | 3.494 | 1 | H11, H15A | C16 | |
| 16 | 4.378 (d, d) | 1 | 21B | — | |
| 17 | 4.28 (br-s) (OH) | 1 | — | — | |

TABLE 4

| | | | | | |
|---|---|---|---|---|---|
| 18 | 3.926 (d; 11.4) | 1 | H20B | — | |
| 19 | 3.740 (d, q; 9.5, 6.2) | 1 | H36, H37 | C15 | |
| 20A | 3.300 (d; 13.2) | 1 | H20B | C23 | |
| 20B | 2.56 | 1 | H18, 20A, 31B | C23 | |
| 21A | 3.15 (d) | 1 | H21B | C24 | |
| 21B | 2.89 (q; 13) | 1 | H16, H21A, H32B | C24 | |
| 22A | 3.114 (d, d; 14.1, 7.0) | 1 | H6, H22B | C27 | C8, C9, C20 |
| 22B | 3.02 (d, d; 14.1, 9.5) | 1 | H6, H22A | C27 | C8, C9, C20 |

TABLE 4-continued

| | | | | | |
|---|---|---|---|---|---|
| 23 | 3.040 (s) | 3 | — | C28 | C3 |
| 24 | 3.04 (OH) | 1 | — | — | |
| 25A | 2.58 | 1 | H25B | C32 | |
| 25B | 1.67 | 1 | H10, H25A, H31B | C32 | |
| 26A | 2.25 (d) | 1 | | C33 | |
| 26B | 1.93 | 1 | | C33 | |
| 27 | 1.93 (m) | 1 | H9, H38, H40 | C29 | C40, C42 |
| 28A | 1.75 | 1 | | C35 | |
| 28B | 1.44 | 1 | H36 | C35 | |

TABLE 5

| | | | | | |
|---|---|---|---|---|---|
| 29A | 1.74 | 1 | | C30 | |
| 29B | 1.65 | 1 | | C30 | |
| 30 | 1.66 | 1 | H39, H41, (35A) | C31 | |
| 31A | 1.66 | 1 | 31B | C36 | |
| 31B | 1.55 | 1 | 20B, 25B, 31A | C36 | |
| 32A | 1.63 | 1 | 32B | C38 | |
| 32B | 1.45 | 1 | 21B, 32A | C38 | |
| 33 | 1.375 (s) | 3 | | C39 | C1, C12, C14 |
| 34 | 1.141 (d; 7.0) | 3 | H11 | C43 | C3, C22 |
| 35A | 1.08 | 1 | H35B | C25 | |
| 35B | 0.95 | 1 | H35A, H36 | C25 | |
| 36 | 1.10 | 1 | H19, H25B, H35B | C26 | |
| 37 | 1.022 (d; 6.2) | 3 | H19 | C41 | C15, C26 |
| 38 | 1.007 (d; 7.0) | 3 | H27 | C42 | C13, C29, C40 |
| 39 | 0.893 (d; 6.2) | 3 | H30 | C34 | C25, C31, C37 |
| 40 | 0.890 (d; 7.3) | 3 | H27 | C40 | C13, C29, C42 |
| 41 | 0.827 (d; 6.6) | 3 | H30 | C37 | C25, C31, C34 |

A and B of the same number represent unequivalent CH$_2$.
(1) Result of measurement of DQF-COSY

TABLE 6

Result of measurement of NOE

| $^1$H | Shift (J) | In residue | Between residue |
|---|---|---|---|
| 1 | 9.62(s) | | |
| 2 | 8.341(d;10.6) | 9 | 21B, 12 |
| 3 | 7.26 | | |
| 4 | 7.25 | 6 | |
| 5 | 7.20 | | |
| 6 | 6.473(d,d;7.0,9.5) | 22A | 11 |
| 7 | 6.46(br-s) | | |
| 8 | 6.398(d;7.9) | 14, 15B, 18 | 10, 23 |
| 9 | 5.463(d,d;9.6,1.8) | 2, 13, 27, 40 | 16 |
| 10 | 5.179(d,d) | 25A | 8 |
| 11 | 5.027(q;7.2) | 34 | 6, 23 |
| 12 | 4.90 | 26A, 26B | 2 |
| 13 | 4.88 | 9,38 | |
| 14 | 4.751(d,d;8,4,3.7) | 8, 15A, 15B | 40 |
| 15A | 4.546(d;11.7) | 14, 15B | 23 |
| 15B | 3.494 | 8, 15A, 14 | |
| 16 | 4.378(d,d) | 21A, 32B | 9 |
| 17 | 4.28(br-s) | | |
| 18 | 3.926(d;11.4) | 20A | 8 |
| 19 | 3.740(d,q;9.5,6.2) | 37 | 35A, 35B |
| 20A | 3.300(d;13.2) | 20B, 31, 18 | |
| 20B | 2.56 | 20A | |
| 21A | 3.15(d) | 16, 21B | |
| 21B | 2.89(q;13) | 21A | 2 |
| 22A | 3.114(d,d;14.1,7.0) | 6, 3 or 4, 23 | |
| 22B | 3.02(d,d;14.1,9.5) | 3 or 4, 23 | |
| 23 | 3.040(s) | 3 or 4 | 11, 34 |

TABLE 7

| | | | |
|---|---|---|---|
| 24 | 3.04 | | |
| 25A | 2.58 | 10, 20A, 31B | |
| 25B | 1.67 | | |

TABLE 7-continued

| | | | |
|---|---|---|---|
| 26A | 2.25(d) | 26B, 12 | |
| 26B | 1.93 | 26A, 12 | |
| 27 | 1.93(m) | 9, 38, 40 | |
| 28A | 1.75 | 28B, 35A | |
| 28B | 1.44 | 28A | |
| 29A | 1.74 | | |
| 29B | 1.65 | | |
| 30 | 1.66 | | |
| 31A | 1.66 | | |
| 31B | 1.55 | 20A | |
| 32A | 1.63 | | |
| 32B | 1.45 | | |
| 33 | 1.375(s) | | |
| 34 | 1.141(d;7.0) | 11 | 23 |
| 35A | 1.07 | 35B, 19 | |
| 35B | 0.96 | 35A, 19 | |
| 36 | 1.09 | | |
| 37 | 1.022(d;6.2) | 19 | |
| 38 | 1.007(d;7.0) | 27, 13 | |
| 39 | 0.893(d;6.2) | | |
| 40 | 0.890(d;7.3) | 9 | |
| 41 | 0.827(d;6.6) | | |

A and B of the same number represent unequivalent CH$_2$.

TABLE 8

Assignment of $^{13}$C and $^1$H peaks

| | δ C | δ H |
|---|---|---|
| Ser | | |
| 1(CO) | 170.2 | — |
| 2(CH) | 52.5 | 4.75 |
| 3(CH2) | 60.7 | 3.49, 4.54 |
| 3-OH | — | |
| 2-NH | — | 6.40 |
| Pip | | |
| 4(CO) | 168.9 | — |
| 5(CH) | 52.5 | 5.18 |
| 6CH2) | 24.4 | 1.67, 2.58 |
| 7(CH2) | 21.5 | 155, 1.66 |
| 8(CH2) | 47.9 | 2.56, 3.30 |
| 8-NH | — | 3.93 |

TABLE 9

| N-Me-Phe | | |
|---|---|---|
| 9(CO) | 171.9 | — |
| 10(CH) | 52.0 | 6.47 |
| 11(CH2) | 33.9 | 3.02, 3.11 |
| 12(C) | 136.6 | — |
| 13,17(CH) | 129.4 | 7.25 |
| 14,16(CH) | 128.3 | 7.26 |
| 15(CH) | 126.7 | 7.20 |
| 18(CH3) | 29.4 | 3.04 |

TABLE 9-continued
N-OH-Ala
| | | |
|---|---|---|
| 19(CO) | 173.6 | — |
| 20(CH) | 50.6 | 5.03 |
| 21(CH3) | 13.0 | 1.14 |
| N-OH | — | 9.62 |
TABLE 10
Pip
| | | |
|---|---|---|
| 22(CO) | 174.3 | — |
| 23(CH) | 51.7 | 4.90 |
| 24(CH2) | 24.2 | 1.93, 2.25 |
| 25(CH2) | 21.3 | 1.45, 1.63 |
| 26(CH2) | 46.1 | 2.89, 3.15 |
| 26-NH | — | 4.38 |
3-OH-Leu
| | | |
|---|---|---|
| 27(CO) | 170.6 | — |
| 28(CH) | 55.0 | 4.88 |
| 29(CH) | 78.9 | 5.46 |
| 30(CH) | 29.4 | 1.93 |
| 31(CH3) | 19.7 | 0.890 |
| 32(CH3) | 14.9 | 1.01 |
| 28-NH | — | 8.34 |
TABLE 11
Side chain
| | | |
|---|---|---|
| 33(CO) | 177.0 | — |
| 34(C) | 76.8 | — |
| 35(C) | 99.2 | — |
| 36(CH2) | 27.8 | 1.65, 1.74 |
| 37(CH2) | 24.1 | 1.44, 1.75 |
| 38(CH) | 39.8 | 1.10 |
| 39(CH) | 71.6 | 3.74 |
| 40(CH3) | 20.0 | 1.375 |
| 41(CH2) | 40.9 | 0.95, 1.08 |
| 42(CH) | 24.7 | 1.66 |
| 43(CH3) | 24.1 | 0.893 |
| 44(CH3) | 21.4 | 0.83 |
| 45(CH3) | 19.3 | 1.02 |
| Others (OH) | | 6.46, 4.28, 3.04 |
Partial structure A [I]
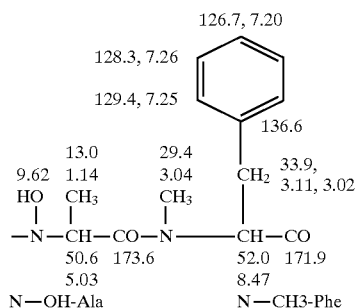
Partial structure B
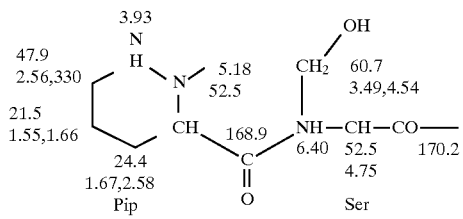
Partial structure C
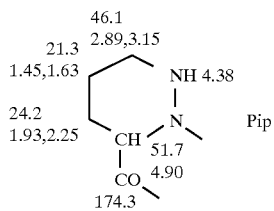

-continued

Partial structure D

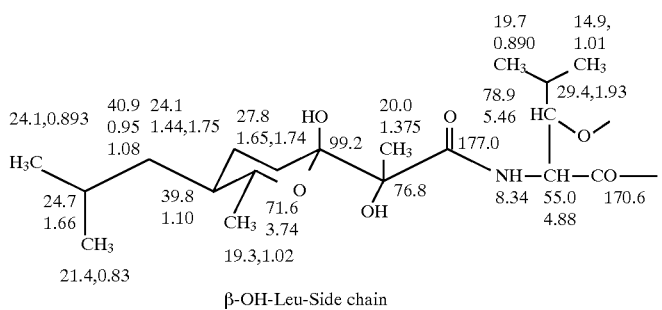

β-OH-Leu-Side chain

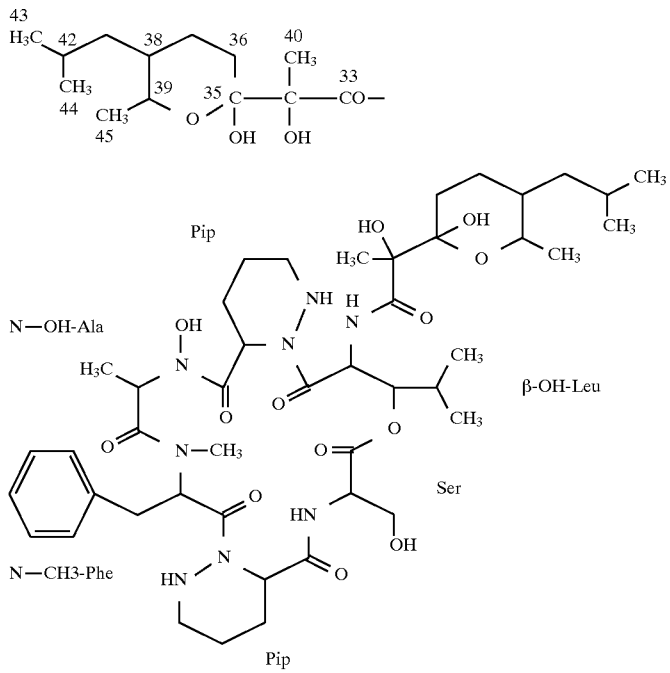

Formulation

Formulation 1 (ointment)

| peptide of the invention | 1 mg |
|---|---|
| Plastibase (manufactured by Taisho Pharmaceutical Co., Ltd.) | 1 g |

After 1 mg of the peptide of the invention was divided finely using a mortar, 1 g of Plastibase was added to the peptide. They are mixed on the mortar sufficiently to prepare an ointment.

Formulation 2 (ointment)

| peptide of the invention | 0.2 mg |
|---|---|
| methanol | 12.5 μl |
| Plastibase (manufactured by Taisho Pharmaceutical Co., Ltd.) | 1 g |

After 0.8 mg of the peptide of the invention was dissolved in 50 μl of methanol, 12.5 μl of the obtained methanol containing the peptide of the invention was mixed with 1 g of Plastibase on the mortar sufficiently to prepare an ointment.

Formulation 3 (liquid preparation)

| peptide of the invention | 0.5 mg |
|---|---|
| DMSO | 0.1 ml |
| 5% by weight of aqueous gum arabic solution | 1.9 ml |

After 0.1 ml of DMSO was added to 0.5 mg of the peptide of the invention to dissolve the peptide, 0.1 ml of the obtained DMSO solution containing the peptide of the invention was added to 1.9 ml of 5% by weight of an aqueous gum arabic solution little by little while stirring to prepare a liquid preparation suspended homogeneously.

Formulation 4 (liquid preparation)

| peptide of the invention | 0.5 mg |
|---|---|
| physiological saline | 2 ml |

A small amount of physiological saline was added to 0.5 mg of the peptide of the invention and the obtained mixture was subjected to ultrasonication to prepare a homogeneous suspension. Physiological saline was added to the suspension to prepare 2 ml of a liquid preparation.

Formulation 5 (liquid preparation)

| peptide of the invention | 25 mg |
|---|---|
| ethanol | 2.5 ml |
| polyoxyethylene hydrogenated castor oil 60 | 1 g |
| physiological saline | 96.5 ml |

After 25 mg of the peptide of the invention was dissolved in 2.5 ml of ethanol, 1 g of polyoxyethylene hardened castor oil 60 was added thereto. The obtained solution was added to 96.5 ml of physiological saline little by little while stirring to prepare a liquid preparation.

Formulation 6 (liquid preparation)

| peptide of the invention | 10 mg |
|---|---|
| macrogol 400 | 50 ml |
| physiological saline | q. s. |

After 10 mg of the peptide of the invention was dissolved in 50 ml of macrogol, physiological saline was added thereto to prepare 100 ml of a liquid preparation.

Pharmacological test

Test 1 is given as a test showing an antimicrobial activity of the peptide of the invention. Tests 3–7 are given as tests showing an antiinflammation activity. Tests 8–10 are given as tests showing a wound-healing activity. Test 11 is given as an acute toxicity test of the peptide of the invention.

Test 1 Antimicrobial activity

A methanol solution of the peptide of the invention (10,000 $\mu$ g/ml) was diluted with sterilized water in amounts that made the final concentrations to be 2,000 $\mu$ g/ml, 500 $\mu$ g/ml, 100 $\mu$ g/ml, 5 $\mu$ g/ml and 1 $\mu$ g/ml respectively to prepare diluted solutions of five stages. A one-ninth amount of each diluted solution was added to a medium for measurement of susceptibility kept at about 50° C. [bacterium: Mueller Hinton Broth (manufactured by Difco Co., Ltd.), mold: 1.5% agar-added glucose peptone medium (manufactured by Nissui Pharmaceutical Co., Ltd.)] and they were mixed sufficiently. Each mixture was pipetted into a Petri dish and solidified to prepare plate media for measurement of susceptibility (the peptide of the invention: 200 $\mu$ g/ml, 50 $\mu$ g/ml, 10 $\mu$ g/ml, 0.5 $\mu$ g/ml and 0.1 $\mu$ g/ml respectively).

As test bacteria, (1) *Staphylococcus aureus* IFO 12732, (2) *Staphylococcus aureus* IID 1677 (methicillin-resistant *S. aureus*; MRSA), (3) *Enterococcus faecalis* IFO 12964 and (4) *Staphylococcus epidermidis* IFO 13889, which are Gram-positive bacteria, (5) *Pseudomonas aeruginosa* IFO 13275 being a Gram-negative bacterium and (6) *Trichophyton mentagrophytes* IFO 6202 being mold were used.

Each test bacterium was cultured in the medium and under the condition shown in Table 12. With respect to the bacteria (1)–(5), bacterium liquids for inoculation were prepared using Mueller Hinton Broth as the medium so that the number of the bacteria was about $10^6$/ml. The mold (6) was floated on a 0.005% sterilized dioctyl sodium sulfosuccinate solution to prepare a bacterium liquid for inoculation so that the number of the bacteria was about $10^6$/ml.

The bacterium liquid for inoculation obtained in this manner was streak-smeared on the plate for measurement of susceptibility in length of about 2 cm with a plastic loop having about 1 mm in inner diameter. The bacteria (1)–(5) were cultured at 35° C. for 18 to 20 hours and the mold (6) was cultured at 25° C. for 7 days.

After culturing the bacterium for a prescribed period of time, the minimum concentration at which the growth of each bacterium was inhibited was determined. It is defined as the minimum inhibitory concentration (MIC, $\mu$ g/ml). The obtained results are shown in Table 13.

TABLE 12

Medium for proliferation and culture condition of each test bacterium

| Test bacterium | Medium for proliferation | Culture condition |
|---|---|---|
| (1)–(4) | Mueller Hinton Broth | 35° C., 18–20 hr |
| (5) | 0.4% Potassium nitrate-added Mueller Hinton Broth | 35° C., 18–20 hr |
| (6) | Potato dextrose agar medium (manufactured by Eiken Chemical Co., Ltd.) | 25° C., until spores were formed |

TABLE 13

Minimum growth inhibition concentration for each bacterium

| Test bacterium | MIC ($\mu$g/ml) |
|---|---|
| (1) *Staphylococcus aureus* IFO 12732 | <0.1 |
| (2) *Staphylococcus aureus* IID 1677 | <0.1 |
| (3) *Enterococcus faecalis* IFO 12964 | <0.1 |
| (4) *Staphylococcus epidermidis* IFO 13889 | <0.1 |
| (5) *Pseudomonas aeruginosa* IFO 13275 | >200 |
| (6) *Trichophyton mentagrophytes* IFO 6202 | >200 |

From these results, the peptide of the invention was found to exhibit a very high antimicrobial activity on Gram-positive bacteria including MRSA causing problems such as nosocomial infection.

Test 3 Effect on Type I allergic inflammation (i) Preparation of rat anti-2,4-dinitrobenzenesulfonic acid-Ascaris suum extract (DNP-As) serum DNP-As was prepared according to the method of Tada and Okumura (Journal of Immunology, 106, 1002 (1971)). An Ascaris suum extract was prepared according to the method of Strejan and Campbell (Journal of Immunology, 98, 893 (1967)) and was bonded to 2,4-dinitrobenzenesulfonic acid (DNP) according to the method of Eisen et al. (Journal of American Chemical Society, 75, 4583 (1953)). One miligram of DNP-As was dissolved in 1 ml of physiological saline on which $10^{10}$ of dead *Bordetella pertussis* were floated and the solution was injected subcutaneously into four footpads of a female rat having weight of about 200 g. Five days after, 0.5 mg of DNP-As was dissolved in 0.5 ml of physiological saline and the solution was injected intramuscularly into the right and left back. Eight days after the first injection, the blood was collected from aorta abdominalis. The serum was separated and used as a rat anti-DNP-As serum. The potency of the antiserum in rat 48-hour homologous PCA reaction was 1:512.

(ii) Effect on rat 48-hour homologous PCA reaction (Type I allergic cutaneous reaction)

The peptide of the invention was suspended in a solution obtained by adding dimethyl sulfoxide in an amount of 5% by weight to 5% by weight of an aqueous gum arabic solution so that the concentration of the peptide was 0.25 mg/ml. Prednisolone was suspended in the solution obtained by adding dimethyl sulfoxide in an amount of 5% by weight to 5% by weight of the aqueous gum arabic solution so that the concentration of prednisolone was 10 mg/ml for a control experiment. The suspensions obtained in this manner were used as test liquids. Male Wister rats having weight of 120 to 200 g were used as test animals.

First, 0.05 ml of an injection obtained by diluting the above-mentioned anti-DNP-As serum 20 times with physiological saline was injected intracutaneously into the back of the rat and thereby the rat was sensitized with the antiserum.

Forty-eight hours after the administration of the antiserum, 2.5 ml/kg of 0.5 wt % of Evans' Blue physiological saline containing 2 mg/ml of DNP-As as the corresponding antigen was administered intraveneously to induce PCA reaction.

With respect to the rats in the group to which the peptide of the invention was administered, 2 ml/kg of the test liquid containing the peptide of the invention (the peptide of the invention: 0.5 mg/kg) was administered intraperitoneally or subcutaneously 24 hours before the induction. With respect to the rats in the group to which prednisolone was administered, 2 ml/kg of the test liquid containing prednisolone (prednisolone: 20 mg/kg) was administered intraperitoneally or subcutaneously 3 hours before the induction.

The leaking pigment at the site where the intracutaneous reaction was caused was extracted and the amount was determined according to the method of Harada et al. (J. Pharm. Pharmacol., 23, 218 (1971)) as follows. The rat was subjected to euthanasia under ether anesthesia one hour after the antigen injection. The skin at PCA reaction site of the rat was incised, minced and immersed in a mixed solution of 3 volumes of a 0.3% (w/v) aqueous sodium sulfate solution and 7 volumes of acetone for 24 hours. The leaking pigment amount was determined. The obtained value represents the leaking pigment amount ($\mu$ g) per the site where the antiserum was injected.

The same procedure as mentioned above was repeated with the exception of using the above-mentioned aqueous gum arabic solution containing dimethyl sulfoxide and no drugs as a control of the test to determine the leaking pigment amount.

Each test was carried out using five rats. The leaking pigment amount ($\mu$ g/site) was expressed in the average of the values obtained with respect to the rats.

Figure 2:
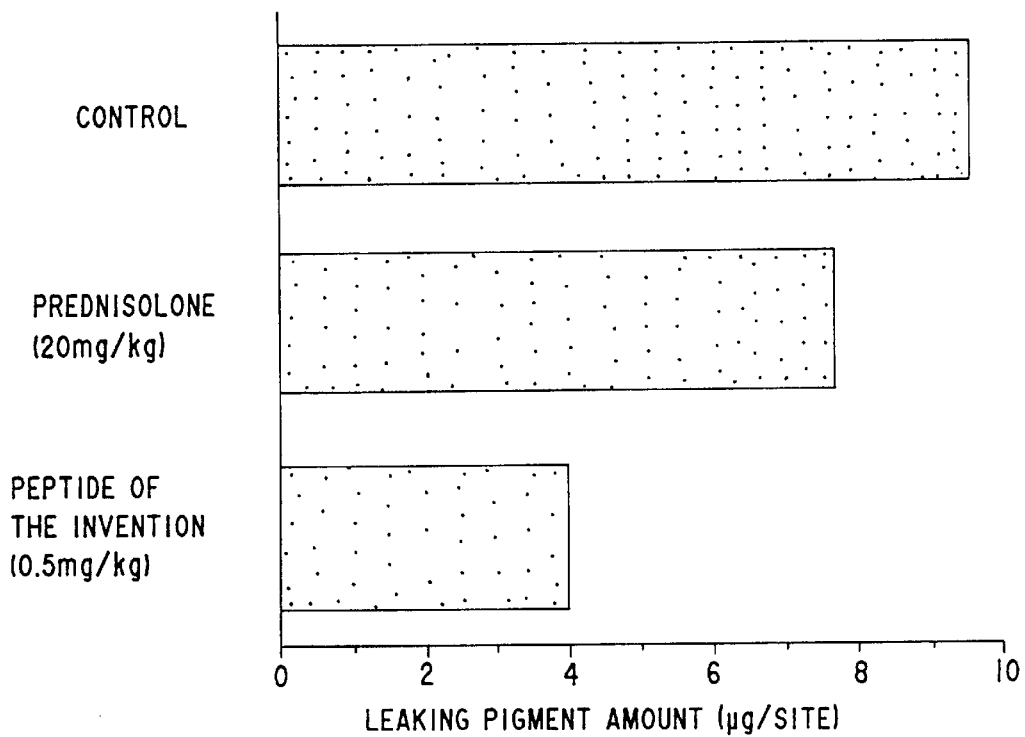
FIG. 2 is a graph showing leaking pigment amounts in rat 48-hour homologous PCA reaction by administering subcutaneously 0.5 mg/kg of the peptide of the invention, 20 mg/kg of prednisolone and a control thereof respectively.

The test results of the intraperitoneal administration are shown in FIG. 1. The test results of the subcutaneous administration are shown in FIG. 2.

As apparent from these figures, the group to which the test liquid containing the peptide of the invention had been administered exhibited a remarkable decrease of the pigment amount leaking to the skin at rat 48-hour homologous PCA reaction site compared with the control group and thereby indicated a high type I allergic inflammation inhibitory activity.

The group to which the test liquid containing the peptide of the invention had been administered exhibited such a remarkable decrease of the pigment amount leaking to the skin at rat 48-hour homologous PCA reaction site compared with the control group, in a smaller dose than that of the test liquid containing prednisolone. Namely, the peptide obtained by the present invention has a higher type I allergic inflammation inhibitory activity than prednisolone.

Test 4 Effect on type III allergic inflammation (i) Preparation of rabbit antiovalbumin serum A rabbit antiovalbumin serum was prepared according to the method of Eda et al. (Folia pharmacologica Japonica, 66, 237 (1970)) by the following method. An antigen solution comprising an emulsion was prepared by mixing equal amounts of 2 mg/ml of a solution of ovalbumin (manufactured by Sigma Chemical Co.) dissolved in physiological saline and complete Freund's adjuvant (manufactured by Difco Co., Ltd.). Into right and left gluteal regions of a male New Zealand white house rabbit having weight of 3 kg was injected 0.5 ml of the antigen solution intramuscularly four times every one week. The blood was collected from carotid artery of the rabbit 7 days after the final injection and only the serum was separated as the rabbit antiovalbumin serum. The potency of the antiserum in rat 4-hour heterologous passive cutaneous anaphylaxis (4-hour heterologous PCA) reaction was 1:32.

(ii) Effect on rat 4-hour heterologous PCA reaction (Type III allergic dermoreaction)

The peptide of the invention was suspended in a solution obtained by adding dimethyl sulfoxide in an amount of 5% by weight to 5% by weight of an aqueous gum arabic solution so that the final concentration of the peptide was 0.25 mg/ml. Prednisolone was suspended in the solution obtained by adding dimethyl sulfoxide in an amount of 5% by weight to 5% by weight of the aqueous gum arabic solution so that the final concentration of prednisolone was 10 mg/ml for a control experiment. The suspensions obtained in this manner were used as test liquids. Male Wister rats having weight of 120 to 200 g were used as test animals.

Into the dorsum of the rat was injected intracutaneously 0.05 ml of an injection obtained by diluting the above-mentioned rabbit antiovalbumin serum four times with physiological saline and thereby the rat was sensitized with the antiserum.

Four hours after the administration of the antiserum, 2.5 ml/kg of 0.5 wt % Evans Blue physiological saline containing 2 mg/ml of ovalbumin as the corresponding antigen was injected intraveneously to induce heterologous PCA reaction for 4 hours.

With respect to the rats in the group to which the peptide of the invention was administered, 2 ml/kg of the test liquid containing the peptide of the invention (the peptide of the invention: 0.5 mg/kg) was administered intraperitoneally or subcutaneously 24 hours before the induction. With respect to the rats in the group to which prednisolone was administered, 2 ml/kg of the test liquid containing prednisolone (prednisolone: 20 mg/kg) was administered intraperitoneally or subcutaneously 3 hours before the induction.

The leaking pigment at the site where the intracutaneous reaction was caused was extracted and the amount was determined according to the method of Harada et al. (J. Pharm. Pharmacol., 23, 218 (1971)) as follows. The rat was subjected to euthanasia under ether anesthesia one hour after the antigen injection. The skin at 4-hour heterologous PCA reaction site of the rat was narrowly cut off and was immersed in a mixed solution of 3 volumes of a 0.3% (w/v) aqueous sodium sulfate solution and 7 volumes of acetone for 24 hours. The leaking pigment amount was determined. The obtained value represents the leaking pigment amount ($\mu$ g) per the site where the rabbit antiovalbumin serum was injected.

The same procedure as mentioned above was repeated with the exception of using the above-mentioned aqueous gum arabic solution containing dimethyl sulfoxide and no drugs as a control of the test to determine the leaking pigment amount.

Each test was carried out using five rats. The leaking pigment amount ($\mu$ g/site) was expressed in the average of the values obtained with respect to the rats.

Figure 3:
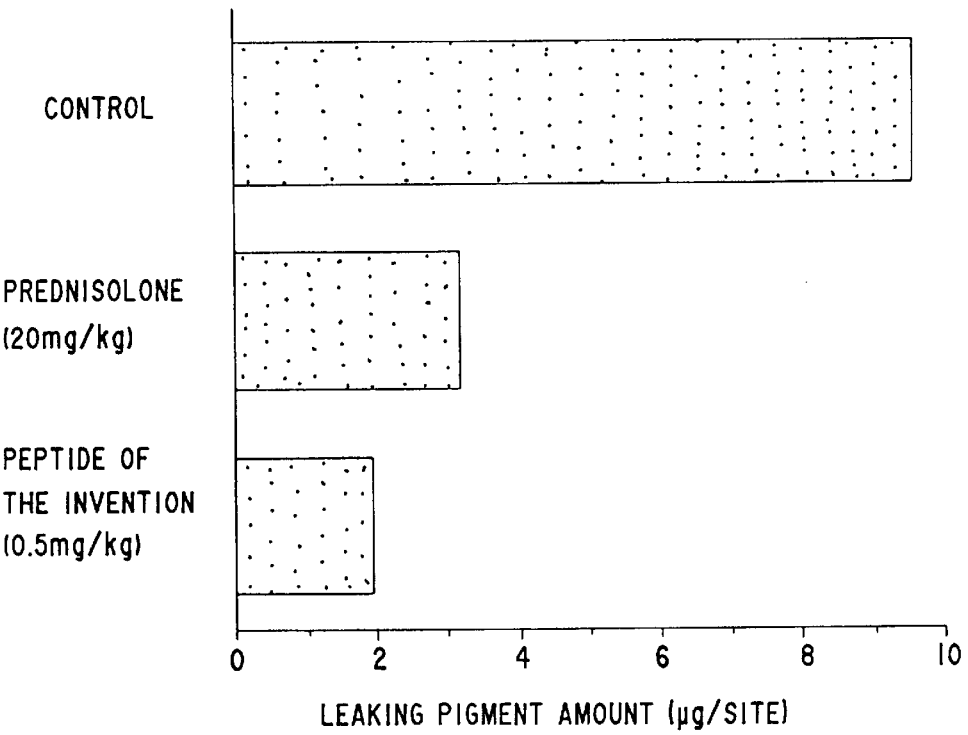
FIG. 3 is a graph showing leaking pigment amounts in rat 4-hour heterologous PCA reaction by administering intraperitoneally 0.5 mg/kg of the peptide of the invetion, 20 mg/kg of prednisolone and a control thereof respectively.
Figure 4:
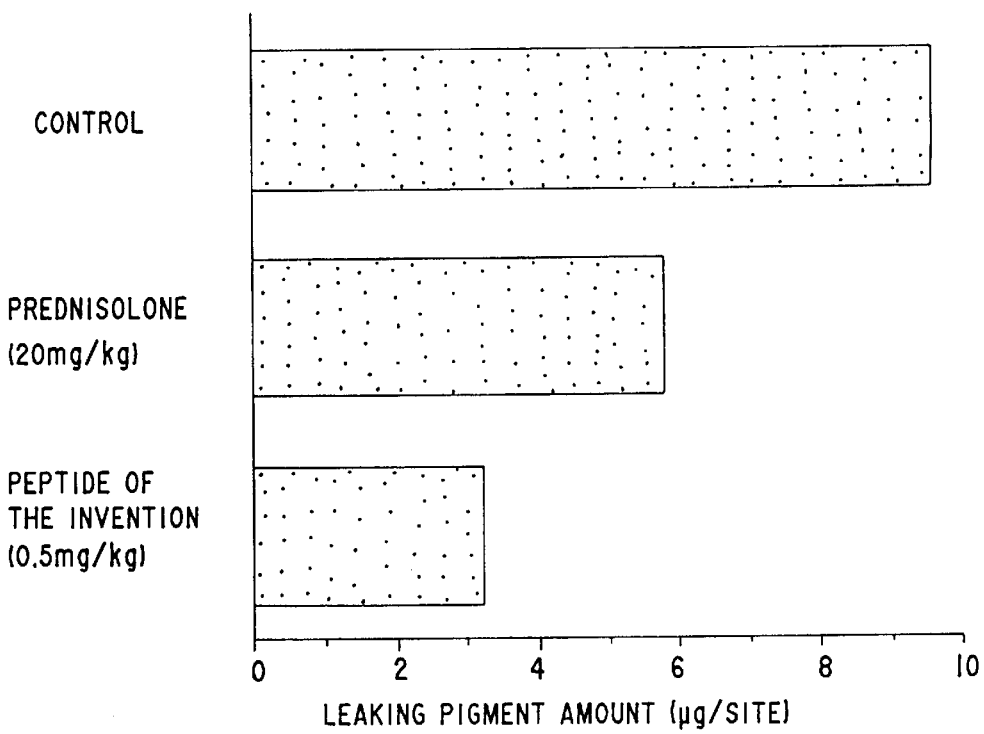
FIG. 4. is a graph showing leaking pigment amounts in rat 4-hour heterologous PCA reaction by administering subcutaneously 0.5 mg/kg of the peptide of the invention, 20 mg/kg of prednisolone and a control thereof respectively.

The test results of the intraperitoneal administration are shown in FIG. 3. The test results of the subcutaneous administration are shown in FIG. 4.

As apparent from these figures, the group to which the test liquid containing the peptide of the invention had been administered exhibited a remarkable decrease of the pigment amount leaking to the skin at rat 4-hour heterologous PCA reaction site compared with the control group and thereby indicated a high allergic inflammation inhibitory activity.

The group to which the test liquid containing the peptide of the invention had been administered exhibited such a remarkable decrease of the pigment amount leaking to the skin at rat 4-hour heterologous PCA reaction site compared with the control group, in a smaller dose than that of the test liquid containing prednisolone. Namely, the peptide of the invention has a higher type III allergic inflammation inhibitory activity than prednisolone.

Test 5 Effect on type IV allergic inflammation

An effect of the peptide of the invention on rat type IV allergic inflammation (tuberculin reaction) was examined by the following method.

First, the peptide of the invention was suspended in a solution obtained by adding dimethyl sulfoxide in an amount of 5% by weight to 5% by weight of an aqueous gum arabic solution so that the final concentration of the peptide was 0.25 mg/ml. Prednisolone was suspended in the solution obtained by adding dimethyl sulfoxide in an amount of 5% by weight to 5% by weight of the aqueous gum arabic solution so that the concentration of prednisolone was 25 mg/ml for a control experiment. The suspensions obtained in this manner were used as test liquids. Male Wister rats having weight of 170 to 250 g were used as test animals.

Tuberculin reaction was induced according to the method of Kuriyama et al. (Folia pharmacologica Japonica, 94, 113–118 (1989)) provided that 2 ml/kg of the test liquid (the peptide of the invention: 0.5 mg/kg, prednisolone: 50 mg/kg) was administered intraperitoneally one hour before the induction. Twenty-four hours after the induction, the degree of erythema was measured according to the Draize's criterion. A reaction site was stamped out with a punch having a diameter of 1.8 cm and the skin weight was measured.

The same procedure as mentioned above was repeated with the exception of using the above-mentioned aqueous gum arabic solution containing dimethyl sulfoxide and no drugs instead of the above-mentioned test liquid as a control of the test.

Each test was carried out using four rats. The degree of erythema and the skin weight were expressed in the averages of the values obtained with respect to the rats.

Figure 5:
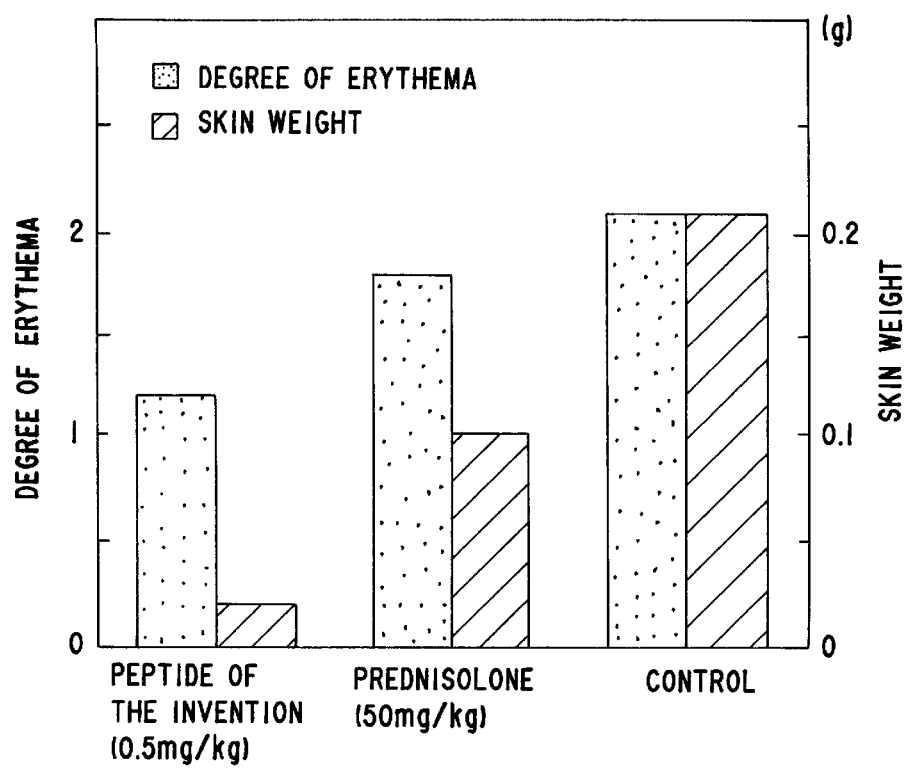
FIG. 5 is a graph showing degrees of erythema and skin weights in rat tuberculin reaction by administering intraperitoneally 0.5 mg/kg of the peptide of the invetion, 50 mg/kg of prednisolone and a control thereof respectively.

The test results are shown in FIG. 5.

As apparent from this figure, the group to which the test liquid containing the peptide of the invention had been administered exhibited a remarkable inhibition of the erythema and a remarkable decrease of the skin weight compared with the control group and the effects were higher than those of the group to which prednisolone had been administered. Namely, the peptide of the invention has a higher inhibitory activity on type IV allergic inflammation (tuberculin reaction) being immune inflammation than prednisolone.

Test 6 Effect on anallergic inflammation

An effect of the peptide of the invention on rat carrageenin footpad edema reaction was examined by the following method.

First, the peptide of the invention was suspended in a solution obtained by adding dimethyl sulfoxide in an amount of 5% by weight to 5% by weight of an aqueous gum arabic solution so that the final concentration of the peptide was 0.25 mg/ml. Aspirin and prednisolone were individually suspended in the solution obtained by adding dimethyl sulfoxide in an amount of 5% by weight to 5% by weight of the aqueous gum arabic solution so that the final concentrations of aspirin and prednisolone were 50 mg/ml and 2.5 mg/ml respectively for control experiments. The suspensions obtained in this manner were used as test liquids. Male Wister rats having weight of 120 to 200 g were used as test animals.

The volume of a right hind leg of the rat was measured with a plethysmometer. Then 0.1 ml of 1% (w/v) carrageenin solution in physiological saline was injected intracutaneously into the right hind footpad of the rat to induce the carrageenin footpad edema reaction. In order to examine a degree of swelling of the right hind footpad of the rat, the volume of the right hind leg of the rat was measured with the plethysmometer every one hour from 1 to 5 hours after the induction of the footpad edema reaction, followed by determining the differences between the volume before the induction of the reaction and the volumes after the induction of the reaction.

With respect to the rats in the group to which the peptide of the invention was administered, 2 ml/kg of the test liquid containing the peptide of the invention (the peptide of the invention: 0.5 mg/kg) was administered intraperitoneally 24 hours before the induction. With respect to the rats in the group to which aspirin was administered, the test liquid containing aspirin (aspirin: 100 mg/kg) was administered intraperitoneally one hour before the induction. With respect to the rats in the group to which prednisolone was administered, 2 ml/kg of the above-mentioned test liquid containing prednisolone (prednisolone: 5 mg/kg) was administered intraperitoneally one hour before the induction.

The same procedure as mentioned above was repeated with the exception of using the above-mentioned aqueous gum arabic solution containing dimethyl sulfoxide and no drugs as a control of the test to examine the degree of swelling of the right hind footpad of the rat.

Each test was carried out using five rats. The degree of swelling of the footpad was expressed in the average of the values obtained with respect to the rats.

Figure 6:
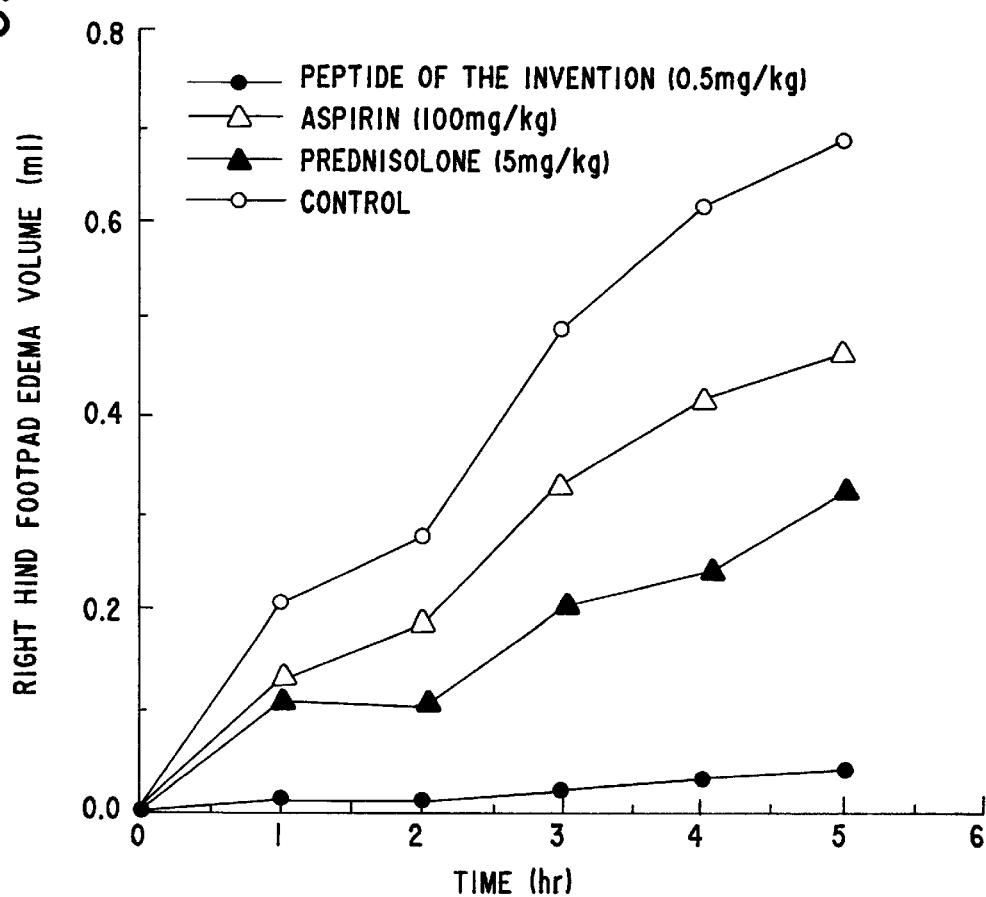
FIG. 6 is a graph showing right hind footpad edema voluem in rat carrageenin edema by administering intraperitoneally 0.5 mg/kg of the peptide of the invention, 100 mg/kg of aspirin, 5 mg/kg of prednisolone and a control thereof respectively.

The test results are shown in FIG. 6.

As apparent from this figure, the group to which the test liquid containing the peptide of the invention had been administered exhibited a remarkable inhibition of the swelling of the right hind footpad compared with the control group and the effect was higher than that of the group to which aspirin or prednisolone had been administered. Namely, the peptide of the present invention has a higher anallergic inflammation inhibitory activity than aspirin and prednisolone.

Test 7 Effect on adjuvant arthritis

An effect of the peptide of the invention on rat adjuvant arthritis was examined by the following method.

First, the peptide of the invention was suspended in a solution obtained by adding dimethyl sulfoxide in an amount of 5% by weight to 5% by weight of an aqueous gum arabic solution so that the final concentration of the peptide was 0.25 mg/ml. Prednisolone was suspended in the solution obtained by adding dimethyl sulfoxide in an amount of 5% by weight to 5% by weight of the aqueous gum arabic solution so that the concentration of prednisolone was 5 mg/ml for a control experiment. The suspensions obtained in this manner were used as test liquids. Male Wistar Lewis rats having weight of 120 to 200 g were used as test animals.

First, 0.1 ml of *Mycobacterium tuberculosis* H37RA (6 mg/ml) suspended in liquid paraffin was injected subcutaneously into a right hind leg of the rat. Then 2 ml/kg/day of the above-mentioned test liquid (the peptide of the invention: 0.5 mg/kg/day, prednisolone: 10 mg/kg/day) was administered intraperitoneally once a day for 22 days after the injection of mycobacterium. The volumes of right and left hind legs of the rat were measured with a plethysmometer. Differences between the volumes before the injection of mycobacterium and those after the injection of mycobacterium were determined. They are defined as degrees of swelling.

The same procedure as mentioned above was repeated with the exception of using the above-mentioned aqueous gum arabic solution containing dimethyl sulfoxide and no drugs instead of the above-mentioned liquid containing the test liquid as a control of the test to examine the degrees of swelling of the right and left hind legs of the rat.

Each test was carried out using seven rats. The degrees of swelling were expressed in the averages of the values obtained with respect to the rats.

Figure 7:
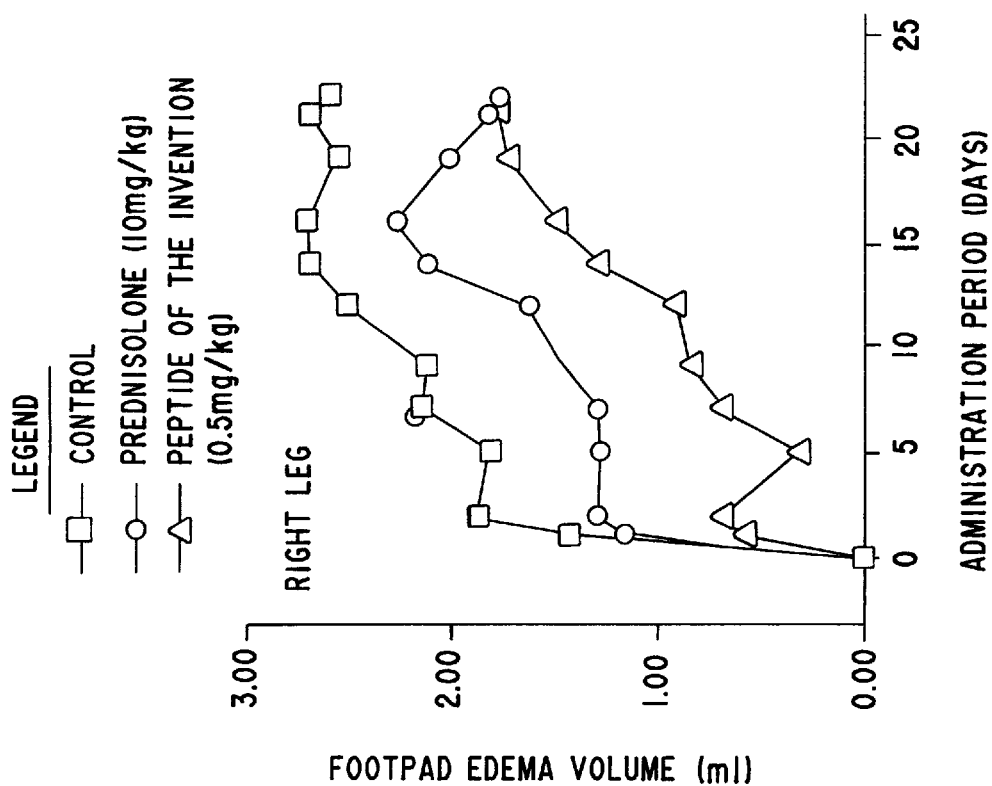
FIGS. 7A and 7B are is a graph showing footpad edma amounts in rat adjuvant arthritis by administering intraperitoneally 0.5 mg/kg of the peptide of the invention, 10 mg/kg of prednisolone and a control thereof respectively.

The test results are shown in FIGS. 7A and 7B are.

As apparent from this figure, the group to which the test liquid containing the peptide of the invention had been administered exhibited remarkable inhibitions of the swellings of the right and left hind footpads compared with the control group and the effect was far higher than that of the group to which prednisolone had been administered. Namely, the peptide of the invention has a higher inhibitory effect on adjuvant arthritis being immune chronic inflammation than prednisolone.

Test 8 Granuloma formation

The peptide of the invention was dissolved in methanol so that the final concentrations of the peptide were $5\mu$ g/ml, $50\mu$ g/ml, $500\mu$ g/ml and $5000\mu$ g/ml respectively. Into a paper disk having a diameter of 8 mm (filter paper for assay of antibiotics manufactured by Advantech Co., Ltd.) was impregnated $20\mu$ l of each methanol solution having the above-mentioned concentration in two parts and then methanol was removed by air-drying (the peptide of the invention: $0.1\mu$ g/disk to $100\mu$ g/disk).

Male Wister rats having weight of 120 to 200 g were used as test animals.

The rat was shaved under ether anesthesia and an incision in length of about 3 cm was formed along a back medial line of the rat with a surgical knife. The above-mentioned paper disk was buried subcutaneously through the incision and then the incision was sutured. After one week, the rat was subjected to euthanasia under ether anesthesia. The paper disk was taken out from the subcutaneous site and the wet weight of formed granulation was measured.

A paper disk was impregnated with $20\mu$ l of methanol containing no peptide of the invention and air-dried. It was used as a control.

The same procedure as mentioned above was repeated with the exception of using a paper disk which had been impregnated with $25\mu$ l of Solcoseryl injection (manufactured by Taiho Pharmaceutical Co., Ltd.) as a reference medicine (Solcoseryl: 1 mg/disk). A paper disk which had been impregnated with $25\mu$ l of physiological saline was used as a control.

Each test was carried out using five rats. The wet weight of the granulation was expressed in the average of the values obtained with respect to the rats.

Figure 8:
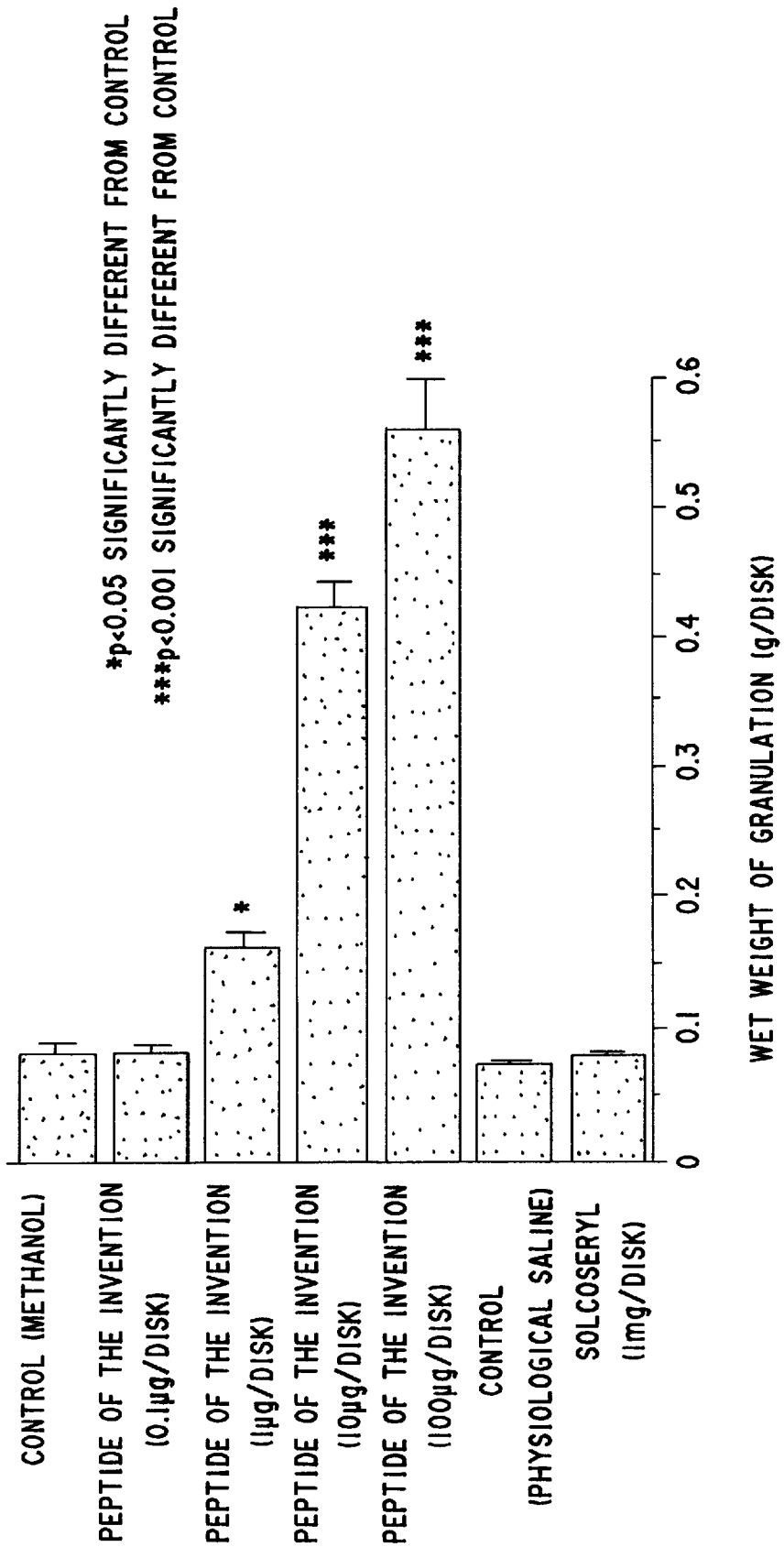
FIG. 8 is a graph showing a relationship between concentrations of the peptide of the invention, a control and a reference medicine, and wet weights of granulation.

The test results are shown in FIG. 8.

As apparent from this figure, the groups in which the disk containing the peptide of the invention of not less than $1\mu$ g/disk had been buried exhibited a remarkable increase of the wet weight of granulation compared with the control groups and the reference group of administering Solcoseryl. Accordingly, the peptide of the invention is recognized to have a cell proliferation effect. The effect of the peptide of the invention of $1\mu$ g/disk is recognized to exceed that of Solcoseryl of 1 mg/disk.

Test 9 Effect on rat incised wound model

The peptide of the invention was dissolved in physiological saline so that the final concentrations of the peptide were $5\mu$ g/ml, $20\mu$ g/mi and $50\mu$ g/ml respectively to prepare test liquids of the peptide of the invention.

Male Wister rats having weight of 250 to 300 g were used as test animals.

The rat was shaved under ether anesthesia and an incision in length of 3 cm was formed crossing a back medial line of the rat perpendicularly with a surgical knife. The incision was sutured at three points at regular intervals. After 3 hours, 0.5 ml of each test liquid (the peptide of the invention: $2.5\mu$ g/incision, $10\mu$ g/incision and $25\mu$ g/incision) was administered subcutaneously around the incision. For 3 days since the day following the incision, 0.5 ml of each test liquid (the peptide of the invention: $2.5\mu$ g/incision, $10\mu$ g/incision and $25\mu$ g/incision) prepared just before using was administered subcutaneously at the incision once a day. Four days after the incision, the rat was subjected to euthanasia under ether anesthesia. After taking out stitches, a skin piece in strip including 2 cm of the center of the incision was cut off. After a connective tissue of the skin piece was removed, a tensile strength of wound of the incision (g/cm) was measured with a rheometer.

As a control, physiological saline was used.

As a reference medicine, 0.5 ml of Solcoseryl injection (Solcoseryl: 20 mg/incision, manufactured by Taiho Pharmaceutical Co., Ltd.) was used.

Each test was carried out using fifteen rats. The tensile strength of wound (g/cm) was expressed in the average of the values obtained with respect to the rats.

Figure 9:
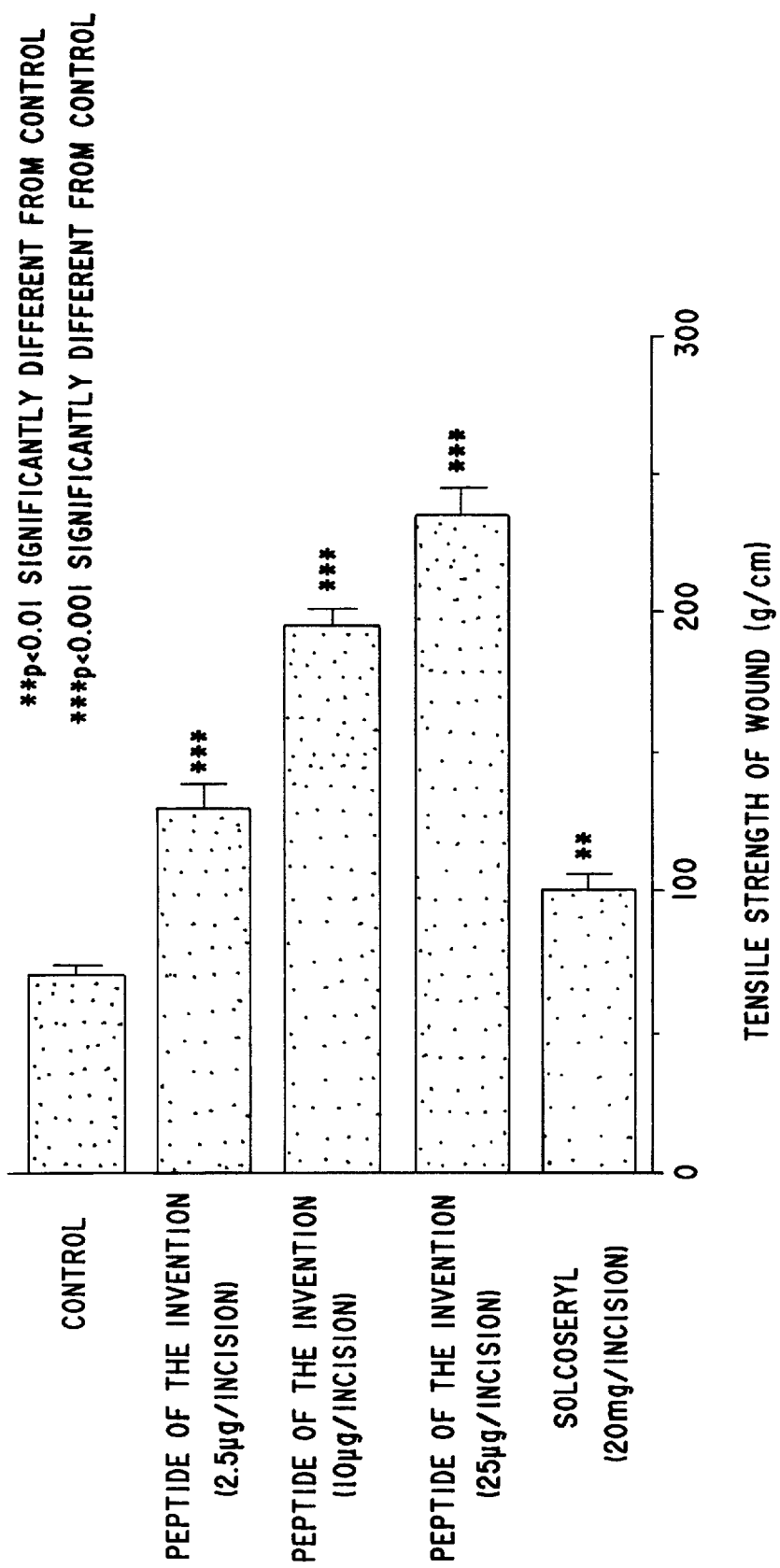
FIG. 9 is a graph showing a relationship between the peptide of the invention, a control and a reference medicine, and tensile strength of wound.

The test results are shown in FIG. 9.

As apparent from this figure, the groups to which the peptide of the invention had been administered exhibited a remarkable increase of the tensile strength of wound compared with the control group and the reference group of administering Solcoseryl. Namely, the peptide of the invention is recognized to exhibit a higher wound-healing accelerating effect than the Solcoseryl injection.

Test 10 Effect on rat skin defect model

The peptide of the invention was mixed with an ointment base (Plastibase manufactured by Taisho Pharmaceutical Co., Ltd.) to prepare an ointment containing 0.02% of the peptide of the invention.

Male Wister rats having weight of 250 to 300 g were used as test animals.

Dexamethasone (1 mg/kg) was administered intraperitoneally to the rat for three days since two days before forming defects. The rat was shaved under ether anesthesia and laid down. The back skin was extended and two skin defects were formed at symmetrical sites with respect to a back medial line of the rat with a punch (16 mm in inner diameter). A sheet of sterilized filter paper (25×25 mm) coated with 50 mg of the ointment (containing $10\mu$ g of the peptide of the invention) prepared just before using was applied per a skin defect. The filter paper was covered with Tegaderm (dressings manufactured by Three M Co., Ltd.) and further with adhesive elastic bandage to fix the filter paper. The ointment was administered once a day till healing. The minor axis and the major axis of each defect were measured with a slide gage from the defect-forming day to the healing day and the area of defect was determined regarding the area as an ellipse.

The same procedure as mentioned above was repeated with the exception of using the ointment base alone (Plastibase manufactured by Taisho Pharmaceutical Co., Ltd.) as a control.

As a reference medicine, 50 mg of Olcenon ointment (tocoretinate: 125μ g/defect, manufactured by Lederle Japan, Ltd.) was used.

Figure 10:
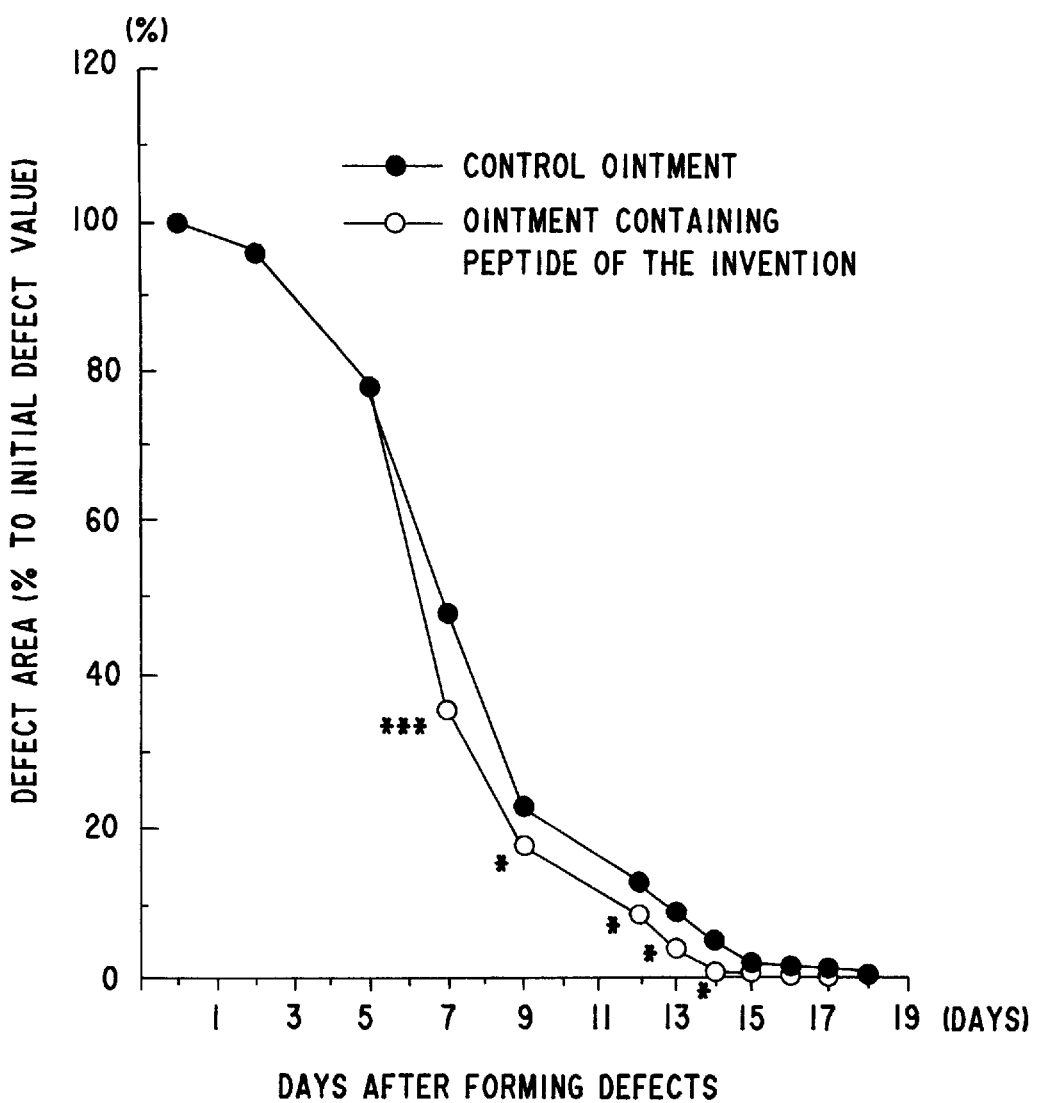
FIG. 10 is a graph showing a relationship between days after forming defects and a defect area with respect to ointment containing the peptide of the invention and control ointment.
Figure 11:
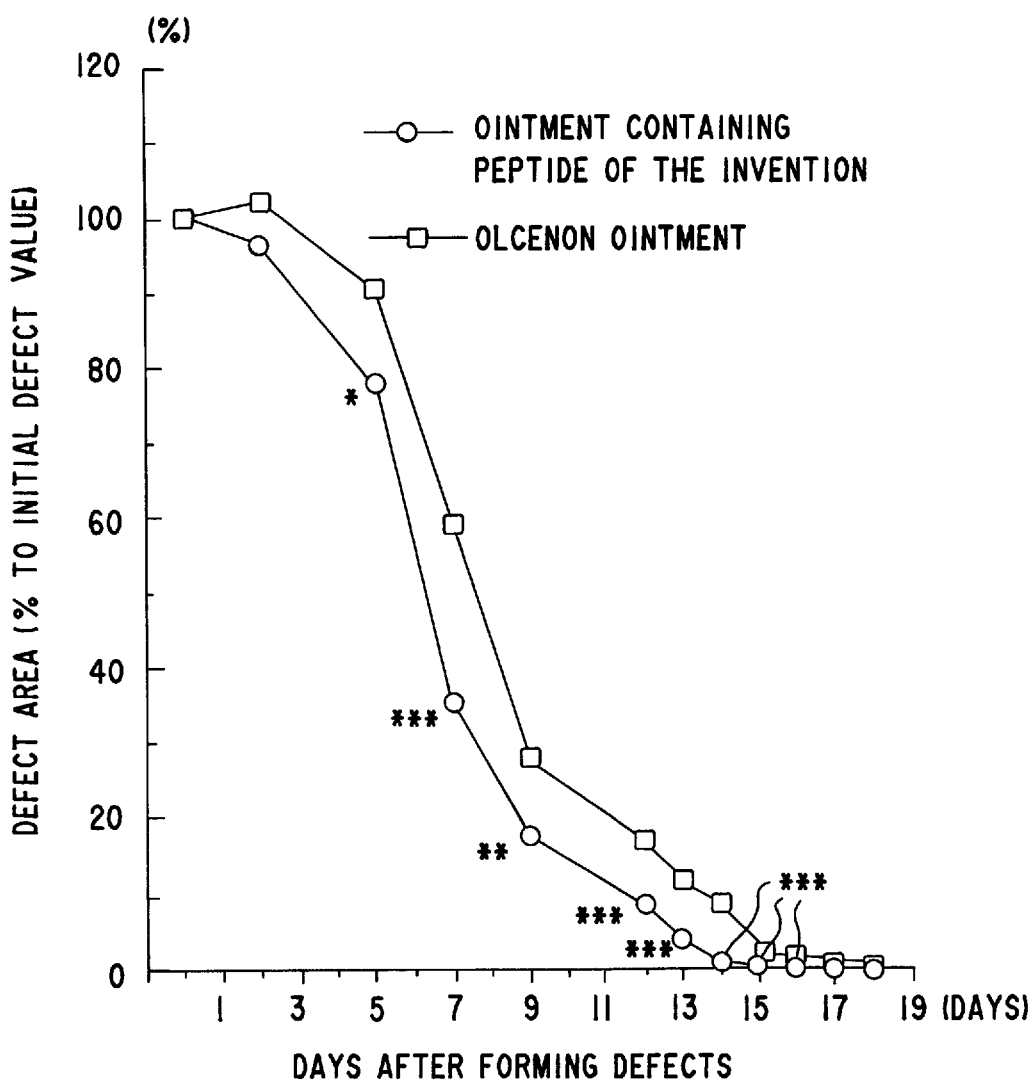
FIG. 11 is a graph showing a relationship between days after forming defects and a defect area with respect to ointment containing the peptide of the invention and reference ointment.

Each test was carried out using seven rats. The area of defect was expressed in the average of the areas of fourteen defects obtained with respect to the rats. The changes of the defect area with time in the test are shown in FIGS. 10 and 11. The complete healing days in the test are shown in Table 15.

TABLE 15

|  | Complete healing (days, ±S.E.) |
| --- | --- |
| Control ointment group | 17 ± 0.7 |
| Ointment containing the peptide of the invention group | 14 ± 0.4** |
| Olcenon ointment group | 18 ± 0.4 |

**p < 0.01 significantly different from control

As apparent from FIGS. 10 and 11, and Table 15, the group to which the peptide of the invention had been administered exhibited a significant effect of reduction in the defect area and shortening of the mean of complete healing days compared with the control group. The group to which the peptide of the invention had been administered also exhibited a remarkable reduction effect in the defect area and shortening of the mean of complete healing days compared with the reference group (Olcenon ointment). Thus the peptide of the invention was recognized to exhibit a remarkable wound-healing accelerating effect.

Test 11 Toxicity test

Toxicity of the peptide of the invention on rats was examined by the following method. First, the peptide of the invention was suspended in a solution obtained by adding dimethyl sulfoxide in an amount of 5% by weight to 5% by weight of aqueous gum arabic solution to prepare a test liquid. Male Wister rats having weight of 120 to 200 g were used as test animals.

Then the test liquid was administered subcutaneously to the rats and the state of the rats was observed. As a result, the rats did not die even if 20 mg/kg of the peptide of the invention was administered to each rat.

Industrial Applicability

The present invention provides a novel peptide represented by the formula [I]. The novel peptide of the present invention exhibits allergic and anallergic inflammation inhibitory, antibacterial and wound-healing effects, and it is useful as an inflammation inhibitor, immunosuppressive agent, antibacterial agent, wound-healing agent, antiulcer agent, and so forth. Accordingly, the present invention also provides therapeutic agents having the above-mentioned pharmacological effects.

We claim:
1. A peptide having the structure:

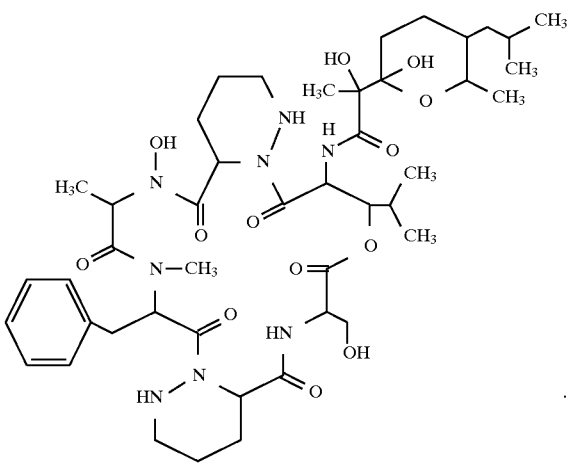

2. An anti-inflammatory pharmaceutical composition comprising the peptide according to claim 1 and a pharmaceutically acceptable carrier.

3. A wound-healing pharmaceutical composition comprising the peptide according to claim 1 and a pharmaceutically acceptable carrier.

4. An anti-ulcer pharmaceutical composition comprising the peptide according to claim 1 and a pharmaceutically acceptable carrier.

5. The peptide according to claim 1, which is obtained by the steps comprising:
   a) culturing the bacteria *Actinomyces S. nobilis* in a culture medium;
   b) separating the bacteria from the culture medium;
   c) extracting said culture medium or said cultured bacteria with an organic solvent to obtain a solvent extract;
   d) performing column chromatography with said solvent extract; and
   e) recovering said peptide.

6. The peptide according to claim 5, wherein the column chromatography is performed using octadecylsilane-modified silica gel.

7. The peptide according to claim 6, wherein the column chromatography is eluted with a solvent which has a polarity between the polarity of a 70% aqueous solution containing a mixed solvent of methanol-acetonitrile (1:1) and the polarity of methanol-acetonitrile-water (19:19:2).

8. The peptide according to claim 7, wherein at least two elution solvents having successively increasing polarity between the polarity of a 70% aqueous solution containing a mixed solvent of methanol-acetonitrile (1:1) and the polarity of methanol-acetonitrile-water (19:19:2) are made to flow in turn through said column.

9. The peptide according to claim 5, wherein the culture medium of step b) is dried prior to extraction.

10. The peptide according to claim 1, which is obtained by the steps comprising:
    a) culturing the bacteria *Actinomyces S. nobilis* in a culture medium;
    b) separating the bacteria from the culture medium;
    c) contacting said culture medium or said cultured bacteria with ammonium sulfate to obtain a precipitate;
    d) extracting said precipitate with an organic solvent to obtain a solvent extract;

e) performing column chromatography with said solvent extract; and f) recovering said peptide.

11. The peptide according to claim 10, wherein the culture medium of step b) is dried and reconstituted prior to treatment with ammonium sulfate.

12. A process for preparing the peptide according to claim 1, comprising the steps of:

a) culturing the bacteria *Actinomyces S. nobilis* in a culture medium;

b) separating the bacteria from the culture medium;

c) extracting said culture medium or said cultured bacteria with an organic solvent to obtain a solvent extract;

d) performing column chromatography with said solvent extract; and e) recovering said peptide.

13. The process according to claim 12, wherein the column chromatography is performed using octadecylsilane-modified silica gel.

14. The process according to claim 13, wherein the column chromatography is eluted with a solvent which has a polarity between the polarity of a 70% aqueous solution containing a mixed solvent of methanol-acetonitrile (1:1) and the polarity of methanol-acetonitrile-water (19:19:2).

15. The process according to claim 14, wherein at least two elution solvents having successively increasing polarity between the polarity of a 70% aqueous solution containing a mixed solvent of methanol-acetonitrile (1:1) and the polarity of methanol-acetonitrile-water (19:19:2) are made to flow in turn through said column.

16. The process according to claim 12, wherein the culture medium of step b) is dried prior to extraction.

17. A process for preparing the peptide according to claim 1, comprising the steps of:

a) culturing the bacteria *Actinomyces S. nobilis* in a culture medium;

b) separating the bacteria from the culture medium;

c) contacting said culture medium or said cultured bacteria with ammonium sulfate to obtain a precipitate;

d) extracting said precipitate with an organic solvent to obtain a solvent extract;

e) performing column chromatography with said solvent extract; and f) recovering said peptide.

18. The process according to claim 17, wherein the culture medium of step b) is dried and reconstituted prior to treatment with ammonium sulfate.

19. The process according to claim 12 or 17, wherein *Actinomyces S. nobilis* is selected from the group consisting of the bacterium deposited at the Institute of Physical and Chemical Research (JCM4274), the bacterium ATCC 19252 deposited in the United States and the bacterium CBS 198.65 deposited in the Netherlands.

* * * * *

UNITED STATES PATENT AND TRADEMARK OFFICE
CERTIFICATE OF CORRECTION

PATENT NO. : 5,858,971

DATED : January 12, 1999

INVENTOR(S) : Fujiwara et al.

It is certified that error appears in the above-identified patent and that said Letters Patent is hereby corrected as shown below:

```
On the title page
Item [22], delete "Oct. 25, 1994" insert therefor
```

-- Oct. 25, 1995 --

Signed and Sealed this

Eighth Day of June, 1999

*Attest:*

Q. TODD DICKINSON

*Attesting Officer*   Acting Commissioner of Patents and Trademarks